United States Patent
Desjardin et al.

(10) Patent No.: US 10,548,859 B2
(45) Date of Patent: *Feb. 4, 2020

(54) METHODS FOR STORING CYSTEAMINE FORMULATIONS AND RELATED METHODS OF TREATMENT

(71) Applicant: Horizon Orphan LLC, Lake Forest, IL (US)

(72) Inventors: Michael Desjardin, Aptos, CA (US); Mark Johnson, Fort Collins, CO (US)

(73) Assignee: Horizon Orphan LLC, Lake Forest, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/402,599

(22) Filed: May 3, 2019

(65) Prior Publication Data

US 2019/0358179 A1    Nov. 28, 2019

Related U.S. Application Data

(63) Continuation of application No. 16/195,481, filed on Nov. 19, 2018, now Pat. No. 10,328,037, which is a continuation of application No. 15/238,037, filed on Aug. 16, 2016, now Pat. No. 10,143,665.

(60) Provisional application No. 62/256,613, filed on Nov. 17, 2015.

(51) Int. Cl.
*A61K 31/145* (2006.01)
*A61K 9/50* (2006.01)

(52) U.S. Cl.
CPC .......... *A61K 31/145* (2013.01); *A61K 9/5026* (2013.01)

(58) Field of Classification Search
None
See application file for complete search history.

(56) References Cited

U.S. PATENT DOCUMENTS

| | | |
|---|---|---|
| 2,809,918 A | 10/1957 | Hermelin |
| 3,835,221 A | 9/1974 | Fulberth |
| 4,324,743 A | 4/1982 | Feuer |
| 4,432,966 A | 2/1984 | Zeitoun |
| 4,728,512 A | 3/1988 | Mehta |
| 4,794,001 A | 12/1988 | Mehta |
| 4,959,306 A | 9/1990 | Kameda |
| 5,225,202 A | 7/1993 | Hodges |
| 5,639,743 A | 6/1997 | Kaswan |
| 5,668,117 A | 9/1997 | Shapiro |
| 6,331,316 B1 | 12/2001 | Ullah |
| 6,794,414 B1 | 9/2004 | Steinman |
| 7,442,720 B2 | 10/2008 | Chan |
| 7,449,451 B2 | 11/2008 | Prasad |
| 7,759,398 B2 | 7/2010 | Chan |
| 7,893,113 B2 | 2/2011 | Chan |
| 8,026,284 B2 | 9/2011 | Dohil |
| 8,129,433 B2 | 3/2012 | Dohil |
| 8,188,151 B2 | 5/2012 | Chan |
| 8,415,398 B2 | 4/2013 | Liang |
| 9,173,851 B1 | 10/2015 | Powell |
| 9,198,882 B2 | 10/2015 | Dohil |
| 9,192,590 B2 | 11/2015 | Dohil |
| 9,233,077 B2 | 1/2016 | Powell |
| 9,511,039 B2 | 12/2016 | Dohil |
| 9,750,708 B2 | 9/2017 | Dohil |
| 9,795,578 B2 | 10/2017 | Dohil |
| 9,814,689 B2 | 11/2017 | Dohil |
| 1,032,803 A1 | 6/2019 | Desjardin |
| 2001/0005716 A1 | 6/2001 | Ullah |
| 2003/0157191 A1 | 8/2003 | Kil |
| 2003/0162747 A1 | 8/2003 | Kil |
| 2004/0033985 A1 | 2/2004 | Chi |
| 2004/0106591 A1 | 6/2004 | Pacioretty |
| 2005/0004075 A1 | 1/2005 | Chi |
| 2005/0008702 A1 | 1/2005 | Faour |
| 2005/0027015 A1 | 2/2005 | Chi |
| 2005/0051103 A1 | 3/2005 | Chi |
| 2005/0089549 A1 | 4/2005 | Chi |
| 2005/0129761 A1 | 6/2005 | Venkata Ramana Rao |
| 2005/0137125 A1 | 6/2005 | Chan |
| 2005/0209441 A1 | 9/2005 | Lile |
| 2005/0245433 A1 | 11/2005 | Chan |
| 2006/0140906 A1 | 6/2006 | Chi |
| 2007/0078113 A1 | 4/2007 | Roth |
| 2007/0172514 A1 | 7/2007 | Chi |
| 2008/0152719 A1 | 6/2008 | Petereit |
| 2008/0276877 A1 | 11/2008 | Chi |
| 2009/0023632 A1 | 1/2009 | Adamson |

(Continued)

FOREIGN PATENT DOCUMENTS

| CN | 101653426 | 2/2010 |
|---|---|---|
| CN | 102077905 | 6/2011 |

(Continued)

OTHER PUBLICATIONS

Arns, W. et al., "Enteric-Coated Mycophenolate Sodium Delivers Bioequivalent MPA Exposure Compared with Mycophenolate Mofetil", ClinTransplant., 19(2):199-206, (2005).
Bacq, Z. et al., "The Action of Cysteamine on Liver Glycogen", Arch Int Physiol., 61(3):417-8, (1953).
Belldina, E. et al., "Steady-State Pharmacokinetics and Pharmacodynamics of Cysteamine Bitartrate in Pediatric Nephropathic Cystinosis Patients", Br J Clin Pharmacol., 56(5):520-5, (2003).
Bendel-Stenzel, M. et al., "Intravenous Delivery of Cysteamine for the Treatment of Cystinosis: Association with Hepatotoxicity", Pediatr Nephrol., 23(2):311-5, (2008).

(Continued)

*Primary Examiner* — Jeffrey T. Palenik
(74) *Attorney, Agent, or Firm* — Chris Marion; Stephanie M. Greer

(57) ABSTRACT

Methods of storing and methods of stabilizing pharmaceutical compositions comprising cysteamine, or a pharmaceutically acceptable salt thereof, are provided. Methods of distributing pharmaceutical compositions comprising cysteamine, or a pharmaceutically acceptable salt thereof, and methods of treating cystinosis also are provided.

18 Claims, 19 Drawing Sheets

(56) References Cited

U.S. PATENT DOCUMENTS

| | | |
|---|---|---|
| 2009/0076166 A1 | 3/2009 | Dohil |
| 2009/0258030 A1 | 10/2009 | Chi |
| 2010/0303870 A1 | 12/2010 | Dohil |
| 2012/0015005 A1 | 1/2012 | Dohil |
| 2012/0015038 A1 | 1/2012 | Dohil |
| 2012/0045506 A1 | 2/2012 | Baer |
| 2012/0237599 A1 | 9/2012 | Dohil |
| 2014/0370085 A1 | 12/2014 | Powell |
| 2015/0290139 A1 | 10/2015 | Powell |
| 2016/0095827 A1 | 4/2016 | Powell |
| 2016/0158170 A1 | 6/2016 | Powell |
| 2016/0331691 A1 | 11/2016 | Dohil |
| 2016/0331704 A1 | 11/2016 | Powell |
| 2016/0331705 A1 | 11/2016 | Dohil |
| 2017/0042845 A1 | 2/2017 | Dohil |
| 2017/0135968 A1 | 5/2017 | Desjardin |
| 2017/0319512 A1 | 11/2017 | Powell |
| 2017/0319513 A1 | 11/2017 | Powell |
| 2017/0319514 A1 | 11/2017 | Powell |

FOREIGN PATENT DOCUMENTS

| | | |
|---|---|---|
| WO | 2002048110 | 6/2002 |
| WO | 2003009699 | 2/2003 |
| WO | 2003024438 | 3/2003 |
| WO | 2003070020 | 8/2003 |
| WO | 2005049002 | 6/2005 |
| WO | 2005063226 | 7/2005 |
| WO | 2005107730 | 11/2005 |
| WO | 2007079670 | 7/2007 |
| WO | 2007082768 | 7/2007 |
| WO | 2009070781 | 6/2009 |
| WO | 2009100950 | 8/2009 |
| WO | 2010103365 | 9/2010 |
| WO | 2012170676 | 12/2012 |
| WO | 2014204881 | 12/2014 |

OTHER PUBLICATIONS

Brok, J. et al., "Intervensions for Paracetamol (Acetaminophen) Overdoses", Cochrane Database Syst Rev., (2):CD003328, (2006).
Butler, J. et al., "Pantethine and Cystamine Deplete Cystine from Cystinotic Fibroblasts via Efflux of Cysteamine-Cysteine Mixed Disulfide", J Clin Invest., 74:411-6, (1984).
Castro, J. et al., "Prevention by Cystamine of Liver Necrosis and Early Biochemical Alterations Induced by Carbon Tetrachloride", Biochem Pharmacol., 21(1):49-52, (1972).
Cheng, G. et al., "Time- and pH-Dependent Colon-Specific Drug Delivery for Orally Administered Diclofenac Sodium and 5-Aminosalicylic Acid", World J Gastroenterol., 10(12):1769-74, (2004).
Cystagon® crysteamine bitartrate delayed-release capsules; Clinical Pharmacology and Biopharmaceutics Review(s), Center For Drug Evaluation and Research, Application No. 203389Orig1s000, pp. 1-58 (2012).
Cystagon® cysteamine bitartrate (Product Information), Alphapharm, (approved Jun. 2008).
Cystagon® cysteamine bitartrate (Summary of Product Characteristics), first approved in 1997, 14 pages, (revised Jun. 2007).
Declaration of Christopher Rubino Under 37 Section C.F.R. §1.132, date of signature Aug. 25, 2015; 8 pages.
Declaration of Ingrid Hoos, Under 37 Section C.F.R. §1.132 date of signature Dec. 12, 2017; 25 pages.
Declaration of Ingrid Hoos, Under 37 Section C.F.R. §1.132, date of signature May 11, 2017; 192 pages.
Declaration of Kurt R. Karst Under 37 Section C.F.R §1.132, date of signature Aug. 12, 2015; 9 pages.
Declaration of Kurt R. Karst Under 37 Section C.F.R §1.132, date of signature Nov. 13, 2015; 3 pages.
Declaration of Mark Johnson Under 37 Section C.F.R. §1.132, date of signature Jul. 26, 2016; 2 pages.
Declaration of Mark Johnson Under 37 Section C.F.R. 1.132, date of signature Sep. 15, 2016; 2 pages.
Dohil, R. et al., "Enteric-Coated Cysteamine for the Treatment of Pediatric Non-Alcoholic Fatty Liver Disease", Aliment Pharmacol Ther., 33(9):1036-44, (2011).
Dohil, R. et al., "Esomeprazole Therapy for Gastric Acid Hypersecretion in Children with Cystinosis", Pediatr Nephrol., 20(12):1786-93, (2005).
Dohil, R. et al., "Long-Term Treatment of Cystinosis in Children with Twice-Daily Cysteamine", J Pediatr., 156(5):823-7, (2010).
Dohil, R. et al., "Pharmacokinetics of Cysteamine Bitartrate Following Intraduodenal Delivery", Fundam Clin Pharmacol., 28(2):136-43, (2014).
Dohil, R. et al., "The Effect of Food on Cysteamine Bitartrate Absorption in Healthy Participants", Clin Pharmacol Drug Dev., 1(4):170-4, (2012).
Dohil, R. et al., "The Evaluation and Treatment of Gastrointestinal Disease in Children with Cystinosis Receiving Cysteamine", J Pediatr., 143(2):224-30, (2003).
Dohil, R. et al., "Treatment of Cystinosis with Delayed-Release Cysteamine: 6-Year Follow-Up", Pediatr Nephrol., 28(3):507-10, (2013).
Dohil, R. et al., "Twice-Daily Cysteamine Bitartrate Therapy for Children with Cystinosis", J Pediatr., 156(1):71-5, (2010).
Dohil, R. et al., "Understanding Intestinal Cysteamine Bitartrate Absorption", J Pediatr., 148(6):764-9, (2006).
Emea (2004). "Cystagon, INN-Mercaptamine bitartrate," Retrieved on Aug. 16, 2017. Retrieved from the internet ,URL: http:/www/ema.europa.eu/docs/en_GB/document_library/EPAR_2004-_Scientific_Discussion/human/000125/WC500037760.pdf>, pp. 1-11.
Emma, F. et al., "Nephropathic Cystinosis: An International Consensus Document", Nephrol Dial Transplant., 29(Suppl 4):iv87-94, (2014).
European Medicines Agency Assessment Report; Procedure EMEA/H/C/002465 for PROCYSBI; published Jun. 27, 2013; Annexes I-III attached; 121 pages; downloaded Sep. 27, 2016.
Felton, L., "Remington: Essentials of Pharmaceutics", Chp. 2, 4, 6, 30, 31 and 32, (2013).
Fidler, M. et al., "Pharmacokinetics of Cysteamine Bitartrate Following Gastrointestinal Infusion", Br J Clin Pharmacol., 63(1):36-40, (2007).
Fischer, P., "Liver Glycogen, X-Rays and Cysteamine", Arch Int Physiol., 62(1):134-6, (Abstract), (1954).
Gangoiti, J. et al., "Pharmacokinetics of Enteric-Coated Cysteamine Bitartrate in Healthy Adults: A Pilot Study", Br J Clin Pharmacol., 70(3):376-382, (2010).
Goodhart, F. et al., "An Evaluation of Aqueous Film-Forming Dispersions for Controlled Release", Pharm Technol., 8(4):64-71, (1984).
Ibie, C., "Development and Evaluation of Oral Solid Dosage Forms for Colonic Delivery of Drugs for the Treatment of Cystinosis", Thesis Robert Gordon University, URL: http:// openair.rgu.ac.uk, (2010).
International Application No. PCT/U52007/002325; International Preliminary Report on Patentability, dated Jul. 29, 2008; 6 pages.
International Application No. PCT/US2007/002325; International Search Report and Written Opinion of the International Searching Authority, dated Oct. 3, 2007; 8 pages.
International Application No. PCT/US2008/085064; International Search Report and Written Opinion of the International Searching Authority, dated Feb. 13, 2009; 6 pages.
International Application No. PCT/US2014/042607; International Preliminary Report on Patentability, dated Dec. 22, 2015; 6 pages.
International Application No. PCT/US2014/042607; International Search Report and Written Opinion of the International Searching Authority, dated Oct. 2, 2014; 8 pages.
Japanese Patent Application No. 2016-521489; Office Action, dated Apr. 17, 2018 (with English translation); 10 pages.
Kleta, R. et al.,"Pharmacological Treatment of Nephropathic Cystinosis with Cysteamine", Expert Opin Pharmacother., 5(11):2255-62, (2004).
Kleta, R., "A Deeper Look Into Cysteamine Absorption For The Treatment Of Cystinosis", J Pediatr., 148(6):718-9, (2006).

(56) References Cited

OTHER PUBLICATIONS

Langman, C. et al., "A Randomized Controlled Crossover Trial with Delayed-Release Cysteamine Bitartrate in Nephropathic Cystinosis: Effectiveness on White Blood Cell Cystine Levels and Comparison of Safety", Clin J Am Soc Nephrol., 7(7):1112-20, (2012).
Langman, C. et al., "Quality of Life is Improved and Kidney Function Preserved in Patients with Nephropathic Cystinosis Treated for 2 years with Delayed-Release Cysteamine Bitartrate", J Pediatr., 165(3)528-33, (2014).
Letter from Raptor Pharmaceuticals Europe B.V. to the European Medicines Agency (EMA) dated Dec. 11, 2015, requesting—for the first time—that the Product Information (i.e., product label) for Procysbi® be revised to reflect a change in storage conditions of the product "from 25° C into 2° C to 8° C (refrigerated)." Exhibit E, 5 pages.
Letter from the European Medicines Agency (EMA) to Raptor Pharmaceuticals dated Jan. 5, 2016, confirming and approving revision of the Procysbi® Product Information to reflect the above-requested change in storage conditions. Exhibit F, 4 pages.
Levtchenko, E. et al., "Strict Cysteamine Dose Regimen is Required to Prevent Nocturnal Cystine Accumulation in Cystinosis", Pediatr Nephrol., 21(1):110-3, (2006).
Manowska, J. et al., "Liver and Muscle Glycogen Contents and Blood Glucose Concentration after AET or MEA Treatment of Adult Male Mice", Folia Biol (Krakow)., 39(1-4):29-31, (1991).
Markello, T. et al., "Improved Renal Function in Children with Cystinosis Treated with Cysteamine", 328(16):1157-62, (1993).
Miners, J. et al., "Mechanism of Action of Paracetomol Protective Agents in Mice In Vivo", Biochem Pharmacol., 33(19):2995-3000, (1984).
Natalie's Wish, Cystinosis Research Foundation, Fall 2004.
Natalie's Wish, Cystinosis Research Foundation, Spring 2004.
Natalie's Wish, Cystinosis Research Foundation, Spring 2005.
Official Journal of the European Union; Summary of European Union decisions on marketing authorisations in respect of medicinal products, Information and Notices, vol. 56, Oct. 25, 2013, Exhibit D, C311/1-3, 5 pages.
Osol, A., "Remington's Pharmaceutical Sciences", 16th ed., pp. 1590-1593, (1980).
Owen, B. et al., "Development of Cysteamine Hydrochloride Pellets for Cystinotic Infants", Eu Hosp Pharm., 3(4):136-42, (1997).
Owen, B. et al., "Film Coating of Cysteamine Hydrochloride Pellets for the Treatment of Cystinosis in Children", Pharm Tech Conf., 20:139-40, (2001).
Owen, B. et al., "Formulation and Processing of Cysteamine Hydrochloride Gastro-Resistant Pellets for the Treatment of Cyslinosis", A thesis submitted to Institute of Pharmacy and Chemistry School of Sciences, University of Sunderland, pp. 1-256, (2000).
Owen, B. et al., "Pilot Scale Manufacture of Gastro-Resistant Cysteamine Hydrocholoride Pellets Using Extrusion Spheronization and Fluid Bed Coating", 15th Pharm Tech Conf., 1:116-119, (1996).
Owen, B. et al., "The Effect of Colloidal Grade of Microcrystalline Cellulose on the Extrusion Rheology and Spheronization of Cysteamine Hydrochloride Formulations", 16th Pharm Tech Conf., pp. 1-8, (1997).
Paoletti, P. et al., "A New Hepato and Radioprotective Agent, 2-Methylpiperazine Dithioformate", 688-96, (1960).
Powell, K. et al., "An Unexpected Problem in the Clinical Assessment of Cystinosis", Pediatr Nephrol., 27(4):687-8, (2012).
Procysbi® crysteamine bitartrate delayed-release capsules; Communication from Raptor Pharmaceuticals, dated Feb. 25, 2016, identifying the change in storage conditions for Procysbi, Exhibit G, 4 pages.
Procysbi® cysteamine bitartrate (Press Release), Horizon Pharma plc Announces Four Poster Presentations on Delayed-Release Capsules at Cystinosis Research Network 2017 Family Conference, 4 pages, (Jul. 14, 2017).
Procysbi™ crysteamine bitartrate delayed-release capsules; Clinical Pharmacology and Biopharmaceutics Review(s), Center for Drug Evaluation and Research, Application No. 203389Orig1s000, compilation from http://www.accessdata.fda.gov/drugsatfda.sub.docs/nda/2013/203389Orig1s000ClinPharmR.pdf, consisting of numbered pp. 1-28, numbered pp. 1-12, and electronic signature page (Reference ID: 3287734); numbered p. 1-10 with electronic signature page (Reference ID: 3261783) and numbered pp. 1-4 with signature page (Reference ID: 3129161) (Available no earlier than Apr. 30, 2013).
Procysbi™ cysteamine bitartrate (Press Release), Horizon Pharma plc Announces Availability in Canada, 2 pages, (Oct. 26, 2017).
Procysbi™ cysteamine bitartrate delayed-release capsules (Highlights of Prescribing Information), Part No. P1304502, Raptor Pharmaceuticals Inc., 13 pages, (revised Apr. 2013).
Procysbi™ cysteamine delayed-release capsules (Press Release), Horizon Pharma plc Announces Health Canada Approval for The Treatment Of Nephropathic Cystinosis, 2 pages, (Jun. 19, 2017).
Schneider, J. et al., "Recent Advances in the Treatment of Cystinosis", J Inherit Metab Dis., 18(4):387-97, (1995).
Schneider, J., "Cystinosis: Crystals to Genes", Pediatr Nephrol., 23:1910, (2008).
Shiratori, K. et al., "Evidence for Significant Role of Gastrin in Cysteamine-Induced Hypersecretion of Gastric Acid", J Clin Gastroenterol., 25(Suppl 1):S84-8, (1997).
Smolin, L. et al., "A Comparison of the Effectiveness of Cysteamine and Phosphocysteamine in Elevating Plasma Cysteamine Concentration and Decreasing Leukocyte Free Cystine in Nephropathic Cystinosis", Pediatr Res., 23(6):616-20, (1988).
Sokal, J. et al., "Glycogenolytic Action of Mercaptoethylamine", Am J Physiol., 196(2):261-4, (1959).
Tennezé, L. et al., "A Study of the Relative Bioavailability of Cysteamine Hydrochloride Cysteamine Bitartrate and Phosphocysteamine in Healthy Adult Male Volunteers", Br J Clin Pharmacol., 47(1):49-52, (1999).
Thoene, J. et al., "Cystinosis Intracellular Cystine Depletion by Aminothiols In Vitro and In Vivo", J Clin Invest., 58(1):180-9, (1976).
U.S. Appl. No. 11/990,869; Non-Final Office Action, dated Feb. 1, 2011; 12 pages.
U.S. Appl. No. 11/990,869; Notice of Allowance, dated May 16, 2011; 8 pages.
U.S. Appl. No. 12/745,504; Non-Final Office Action, dated Mar. 2, 2011; 16 pages.
U.S. Appl. No. 13/399,900; Final Office Action, dated Jun. 2, 2014; 12 pages.
U.S. Appl. No. 13/399,900; Non-Final Office Action, dated Nov. 6, 2012; 5 pages.
U.S. Appl. No. 13/399,900; Non-Final Office Action, dated Sep. 18, 2013; 8 pages.
U.S. Appl. No. 13/399,900; Notice of Allowance, dated Mar. 4, 2013; 9 pages.
U.S. Appl. No. 14/306,303; Examiner-Initiated Interview Summary, dated Dec. 3, 2015; 1 page.
U.S. Appl. No. 14/306,303; Notice of Allowance dated, Dec. 3, 2015; 3 pages.
U.S. Appl. No. 14/751,639; Applicant-Initiated Interview Summary, dated Sep. 24, 2015; 3 pages.
U.S. Appl. No. 14/751,639; Notice of Allowance, dated Sep. 24, 2015; 16 pages.
U.S. Appl. No. 14/751,639; Preinterview First Office Action, dated Jul. 23, 2015; 4 pages.
U.S. Appl. No. 15/042,823; Applicant-Initiated Interview Summary, dated Sep. 20, 2016; 4 pages.
U.S. Appl. No. 15/042,823; Final Office Action, dated Sep. 29, 2017; 15 pages.
U.S. Appl. No. 15/042,823; Non-Final Office Action, dated Dec. 15, 2016; 13 pages.
U.S. Appl. No. 15/042,823; Non-Final Office Action, dated May 2, 2016; 12 pages.
U.S. Appl. No. 15/220,308; Applicant-Initiated Interview Summary, dated Sep. 20, 2016; 4 pages.
U.S. Appl. No. 15/220,308; Final Office Action, dated Sep. 27, 2017; 28 pages.

(56) References Cited

OTHER PUBLICATIONS

U.S. Appl. No. 15/220,308; First Action Interview—Office Action Summary, dated Feb. 23, 2017; 4 pages.
U.S. Appl. No. 15/220,308; Preinterview First Office Action, dated Oct. 20, 2016; 6 pages.
U.S. Appl. No. 15/220,693; Non-Final Office Action, dated Oct. 6, 2016; 6 pages.
U.S. Appl. No. 15/220,693; Notice of Allowance, dated Apr. 28, 2017; 8 pages.
U.S. Appl. No. 15/220,693; Notice of Allowance, dated Jan. 30, 2017; 7 pages.
U.S. Appl. No. 15/224,414; Non-Final Office Action, dated Oct. 11, 2016; 7 pages.
U.S. Appl. No. 15/224,414; Notice of Allowance, dated Feb. 3, 2017; 7 pages.
U.S. Appl. No. 15/224,414; Notice of Allowance, dated Jun. 27, 2017; 8 pages.
U.S. Appl. No. 15/238,037; Advisory Action, dated Apr. 26, 2017; 3 pages.
U.S. Appl. No. 15/238,037; Examiner-Initiated Interview Summary, dated Jun. 12, 2017; 1 page.
U.S. Appl. No. 15/238,037; Final Office Action, dated Dec. 20, 2017; 8 pages.
U.S. Appl. No. 15/238,037; Final Office Action, dated Feb. 13, 2017; 7 pages.
U.S. Appl. No. 15/238,037; Non-Final Office Action, dated Jun. 12, 2017; 8 pages.
U.S. Appl. No. 15/238,037; Non-Final Office Action, dated Oct. 7, 2016; 9 pages.
U.S. Appl. No. 15/238,037; Notice of Allowance, dated Jun. 27, 2018; 7 pages.
U.S. Appl. No. 15/238,037; Notice of Allowance, dated Oct. 1, 2018; 26 pages.
U.S. Appl. No. 15/336,405; Non-Final Office Action, dated Dec. 30, 2016; 6 pages.
U.S. Appl. No. 15/336,405; Notice of Allowance, dated Jun. 23, 2017; 8 pages.
U.S. Appl. No. 15/336,405; Notice of Allowance, dated Mar. 13, 2017; 7 pages.
U.S. Appl. No. 15/656,531; Final Office Action, dated Jun. 13, 2018; 34 pages.
U.S. Appl. No. 15/656,531; Non-Final Office Action, dated Aug. 23, 2017; 20 pages.
U.S. Appl. No. 15/656,570; Final Office Action, dated Jun. 13, 2018; 34 pages.
U.S. Appl. No. 15/656,570; Non-Final Office Action, dated Aug. 23, 2017; 22 pages.
U.S. Appl. No. 15/656,579; Final Office Action, dated Jun. 13, 2018; 34 pages.
U.S. Appl. No. 15/656,579; Non-Final Office Action, dated Aug. 23, 2017; 20 pages.
U.S. Appl. No. 16/195,481; Examiner-Initiated Interview Summary, dated Feb. 6, 2019; 1 page.
U.S. Appl. No. 16/195,481; Notice of Allowance, dated Feb. 6, 2019; 8 pages.
Van Cauwenberge, H. et al., "Carbohydrate Metabolism, Adrenal Cortex and Sulfur Radio-Protectors", Annal Endocrinol., 15:645-50, (Abstract), (1954).
Van De Brug, F. et al., "Contribution of Gastrin to Cysteamine-Induced Gastric Acid Secretion in Rats", Life Sci., 52(23):1861-7, (1993).
Van Stralen, K. et al., "Improvement in the Renal Prognosis in Nephropathic Cystinosis", Clin J Am Soc Nephrol., 6(10):2485-91, (2011).
Wang, X. et al., "Cerebral PET Imaging and Histological Evidence of Transglutaminase Inhibitor Cystamine Induced Neuroprotection in Transgenic R6/2 Mouse Model of Huntington's Disease", J Neur Sci., 231(1-2):57-66, (2005).
Wen, H. et al., "Oral Controlled Release Formulation Design and Drug Delivery", Theory to Practice, John Wiley & Sons, Inc., p. 3, (2010).
Zhou, D. et al., "Understanding Biopharmaceutics Properties for Pharmaceutical Product Development and Manufacturing I-Oral Absorption and the Biopharmaceutics Classification System", J Valid Tech., 15(4):62-72, (2009).

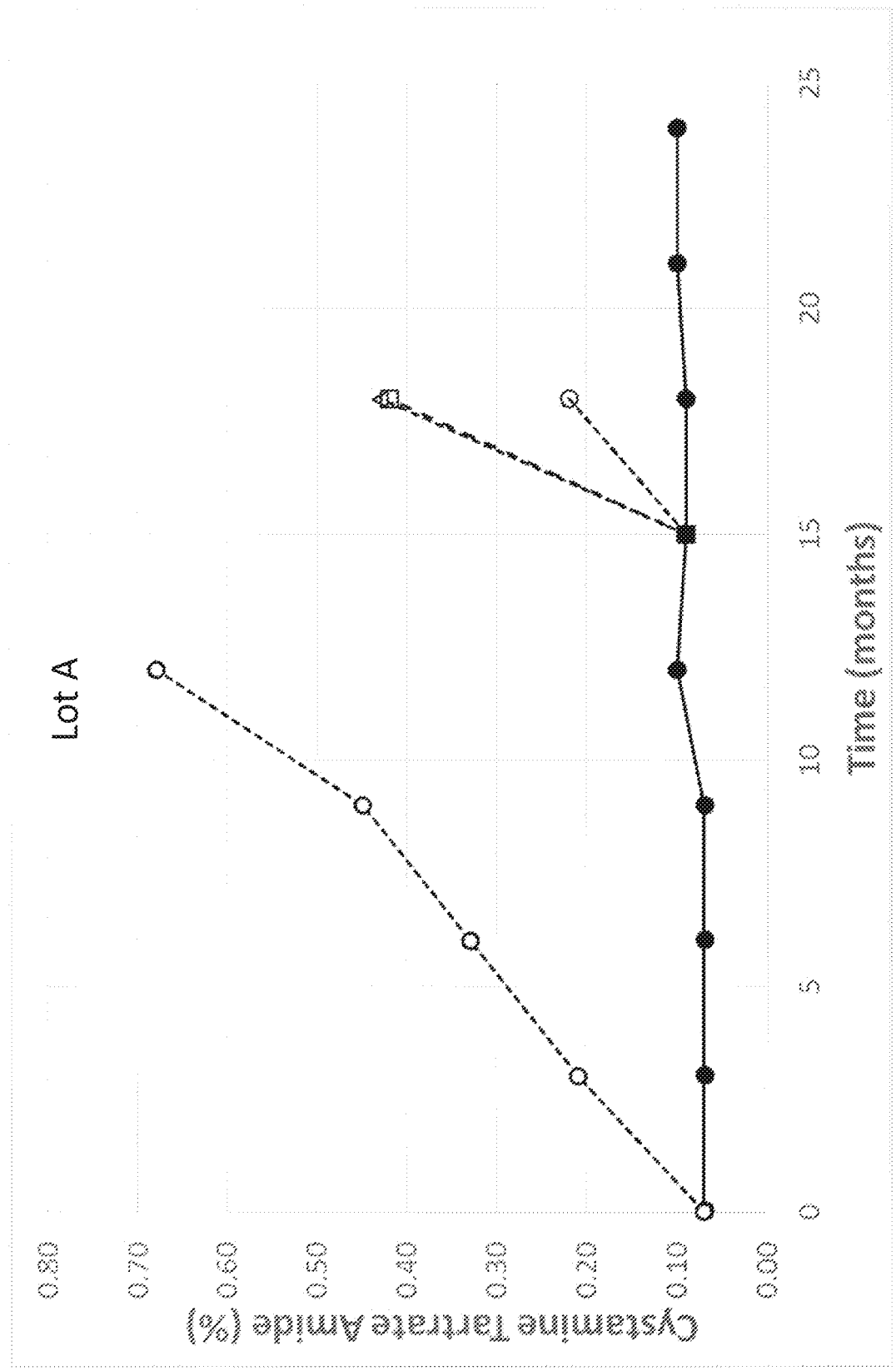

METHODS FOR STORING CYSTEAMINE FORMULATIONS AND RELATED METHODS OF TREATMENT

The present application is a continuation of U.S. application Ser. No. 16/195,481, filed Nov. 19, 2018, now U.S. Pat. No. 10,328,037, which is a continuation of U.S. application Ser. No. 15/238,037, filed Aug. 16, 2016, now U.S. Pat. No. 10,143,665, which claims priority to and benefit of U.S. Provisional Application No. 62/256,613, filed Nov. 17, 2015, the disclosures of which are hereby incorporated by reference as if written herein in their entireties.

BACKGROUND

Cystinosis is a rare, autosomal recessive disease caused by intra-lysosomal accumulation of the amino acid cysteine within various tissues, including the spleen, liver, lymph nodes, kidney, bone marrow, and eyes. Nephropathic cystinosis is associated with kidney failure that necessitates kidney transplantation. A specific treatment for nephropathic cystinosis is the sulfhydryl agent cysteamine. Cysteamine has been shown to lower intracellular cystine levels, thereby reducing the rate of progress of kidney failure in children.

Cysteamine, and pharmaceutically acceptable salts thereof, may also be administered for the treatment of other metabolic and neurodegenerative diseases, including non-alcoholic fatty liver disease (NAFLD), non-alcoholic steatohepatitis (NASH), Huntington's disease, Parkinson's disease, Rett Syndrome, cystic fibrosis, and others; used as free radical and radioprotectants; used as hepato-protectant agents.

Enterically-coated cysteamine compositions for increasing delivery of cysteamine to the small intestine and resulting in less frequent dosing compared to non-enteric-coated cysteamine have been described. See, e.g., WO 2014/204881, WO 2007/089670, and U.S. Pat. Nos. 8,026,284, 9,198,882, 9,192,590, 9,173,851, and 9,233,077.

In some cysteamine pharmaceutical compositions, cysteamine is not chemically stable and degrades into several impurities over time.

SUMMARY OF THE DISCLOSURE

The present disclosure provides methods of storing pharmaceutical compositions comprising cysteamine, or a pharmaceutically acceptable salt thereof, wherein the pharmaceutical composition is stored at refrigerated temperatures (e.g., 2° C.-8° C.) up to 24 months, or longer, and compositions that have been stored in such a manner that have fewer impurities than when stored at 25° C., and methods for using the same. In various embodiments, the disclosure provides a method of storing a pharmaceutical composition, comprising storing the pharmaceutical composition at a temperature of between about 2° C. and about 8° C., wherein the pharmaceutical composition comprises cysteamine, or a pharmaceutically acceptable salt thereof.

In one embodiment, the disclosure provides a method of stabilizing a pharmaceutical composition, comprising storing the pharmaceutical composition at a temperature of between about 2° C. and about 8° C., wherein the pharmaceutical composition comprises cysteamine, or a pharmaceutically acceptable salt thereof.

Also provided is a method of distributing a pharmaceutical composition, comprising storing the pharmaceutical composition at a temperature of between about 2° C. and about 8° C. prior to dispensing to a health care provider or a patient, wherein the pharmaceutical composition comprises cysteamine, or a pharmaceutically acceptable salt thereof.

Further contemplated is a method of treating a disease or disorder, comprising administering a pharmaceutical composition comprising cysteamine, or a pharmaceutically acceptable salt thereof to a subject in need thereof, wherein the pharmaceutical composition has been stored at a temperature of between about 2° C. and about 8° C. prior to administration. Exemplary diseases or disorders contemplated herein include, but are not limited to, cystinosis, fatty liver disease, a thrombotic disease, an MECP-2 related disorder, an inherited mitochondrial disease, a neurological disease or disorder, inflammation and cancer. Additional indications contemplated are set out in the Detailed Description.

In various embodiments of the methods, the pharmaceutical composition further comprises one or more materials that provide increased delivery of cysteamine to the small intestine. In one embodiment, a material that provides increased delivery of cysteamine to the small intestine comprises an enteric coating. Exemplary enteric coatings contemplated comprise a coating selected from the group consisting of polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers formed from methyl acrylate, ethyl acrylate, methyl methacrylate, and/or ethyl methacrylate with copolymers of acrylic and methacrylic acid esters. In one embodiment, the enteric coating comprises poly(methacrylic acid co-ethyl acrylate) 1:1 (Eudragit L 30-D-55).

In various embodiments of the methods, the pharmaceutical composition comprises a pharmaceutically acceptable salt of cysteamine, and the pharmaceutically acceptable salt of cysteamine is cysteamine bitartrate.

It is also contemplated that the pharmaceutical composition comprises a solid composition. In one embodiment, the pharmaceutical composition comprises a unit dose of about 25 mg cysteamine or of about 75 mg cystemine.

In various embodiments, the pharmaceutical composition comprises enteric coated beads. In various embodiments, the pharmaceutical composition is a pharmaceutical dosage form that includes a plurality of cysteamine beads, the beads including a core particle including cysteamine or a pharmaceutically acceptable salt thereof and a pharmaceutically acceptable excipient, and an enteric membrane surrounding the core particle, wherein the plurality of beads is characterized by a distribution of particle sizes.

In one embodiment, the particle sizes of the beads are in a range of about 0.7 mm to about 2.5 mm, or about 0.7 mm to about 2.8 mm, or about 0.8 mm to about 1.7 mm. For example, the target bead size can be up to 2.5 mm with no more than 10 percent variation over this size, to a maximum size of 2.8 mm. In one embodiment, the enteric membrane on the beads is present in an amount in a range of about 20% to 40%, or about 20% to about 25%, or about 25% to about 35% as measured by the weight gain compared to the uncoated particle cores, or in a range of about 25% to about 31% weight gain, or about 27% to about 31% weight gain, or about 28.5% to about 31% weight gain, based on the weight of the uncoated particle cores.

In various embodiments, the bead formulation comprises a plurality of cysteamine beads, the beads comprising a core particle comprising, cysteamine or a pharmaceutically acceptable salt thereof, such as cysteamine bitartrate, a filler, a binder and an enteric membrane surrounding the core, wherein the plurality of beads is characterized by a distribution of particle sizes in a range of about 0.7 mm to about 2.8 mm; wherein the enteric membrane is present in an amount in a range of about 20% to about 40% based on the weight of the bead core particles; wherein the formulation is a delayed release formulation having an enteric membrane that begins to dissolve within a pH range of about 4.5 to about 6.5, and wherein the beads are disposed in a capsule shell.

In further embodiments of the methods above, the pharmaceutical composition is stored at a temperature of between about 2° C. and about 8° C. for up to 1 month, between about 1 month and about 6 months, between about 6 months and about 12 months, between about 12 month and about 15 months, between about 15 months and about 18 months, between about 18 months and about 21 months, between about 21 months and about 24 months, between about 24 months and about 36 months, or between about 36 months and about 39 months. In various embodiments, the pharmaceutical composition is stored at a temperature of between about 2° C. and about 8° C. for 1 month, 6 months, 12 months, 15 months, 18 months, 21 months, 24 months, 36 months, or 39 months.

The methods herein may further comprise storing the pharmaceutical composition at a temperature of between about 20° C. and about 25° C. and a relative humidity of 60% for up to 4 months.

In various embodiments, the pharmaceutical composition is stable through 12, 15, 18, 21 or 24 months at 2° C.-8° C. storage. In various embodiments, the pharmaceutical composition is stable through 24 months at 2° C.-8° C. storage. In various embodiments, the pharmaceutical composition is stable after storage at a temperature of 2° C.-8° C. for up to 15 months followed by excursions of up to 3 months at 25° C./60% RH, 30° C./65% RH, or 30° C./75% RH (18 months of total storage time).

In various embodiments of the methods, the amount of 2-hydroxythiomorpholine present in the pharmaceutical composition, relative to the amount of cysteamine, or a pharmaceutically acceptable salt thereof, present in the pharmaceutical composition, is less that 0.5%. In some embodiments, the amount of 2-hydroxythiomorpholine present in the pharmaceutical composition, relative to the amount of cysteamine, or a pharmaceutically acceptable salt thereof, present in the pharmaceutical composition, is less than or equal to the amount of 2-hydroxythiomorpholine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In various embodiments of the methods above, the amount of cystamine present in the pharmaceutical composition, relative to the amount of cysteamine, or a pharmaceutically acceptable salt thereof, present in the pharmaceutical composition, is less that 4%. In certain embodiments, the amount of cystamine present in the pharmaceutical composition, relative to the amount of cysteamine, or a pharmaceutically acceptable salt thereof, present in the pharmaceutical composition, is less than or equal to the amount of cystamine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

It is contemplated that the amount of cystamine tartrate amide present in the pharmaceutical composition, relative to the amount of cysteamine, or a pharmaceutically acceptable salt thereof, present in the pharmaceutical composition, is less than 0.5%. In various embodiments, the amount of cystamine tartrate amide present in the pharmaceutical composition, relative to the amount of cysteamine, or a pharmaceutically acceptable salt thereof, present in the pharmaceutical composition, is less than or equal to the amount of cystamine tartrate amide present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

The methods also provide that the amount of 2-hydroxymethylthiazolidine present in the pharmaceutical composition, relative to the amount of cysteamine, or a pharmaceutically acceptable salt thereof, present in the pharmaceutical composition is less than 0.05%. In various embodiments, the amount of 2-hydroxymethylthiazolidine present in the pharmaceutical composition, relative to the amount of cysteamine, or a pharmaceutically acceptable salt thereof, present in the pharmaceutical composition, is less than or equal to the amount of 2-hydroxymethylthiazolidine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In various embodiments, the total amount of 2-hydroxymethylthiazolidine, cystamine, cystamine tartrate amide, and 2-hydroxymethylthiazolidine present in the pharmaceutical composition, relative to the amount if cysteamine, or a pharmaceutically acceptable salt thereof, present in the pharmaceutical composition, is less than or equal to the total amount of 2-hydroxymethylthiazolidine, cystamine, cystamine tartrate amide, and 2-hydroxymethylthiazolidine present in the pharmaceutical acceptable salt thereof, present in the pharmaceutical composition, after storage at a temperature of between about 20° C. and about 25° C. and relative humidity of 60% for the same duration.

In another aspect, the present disclosure provides methods of treating a disease or disorder by administering to a subject in need thereof a pharmaceutical composition comprising cysteamine, or a pharmaceutically acceptable salt thereof, wherein the pharmaceutical composition has been stored at a temperature of between about 2° C. and about 8° C. prior to administration. Disease or disorders contemplated herein are described in more detail in the Detailed Description.

Also provided is a method of treating cystinosis, comprising administering a pharmaceutical composition comprising cysteamine, or a pharmaceutically acceptable salt thereof, wherein the pharmaceutical composition has been stored at a temperature of between about 2° C. and about 8° C. prior to administration. In various embodiments, the cystinosis is nephropathic cystinosis.

In various embodiments, the pharmaceutical composition is formulated to provide white blood cell cystine suppression with a 12 hour level below 1 nmol½ cystine/mg protein.

In various embodiments, each dose of cysteamine is about 0.5-1.0 g/m2 body surface area. In various embodiments, the total daily dose of cysteamine is about 1.3 g/m2 body surface area or less. In various embodiments, the composition is administered less than four times daily, e.g., one, two or three times a day. In various embodiments, the composition is administered twice daily, or every 12 hours.

In various embodiments, the composition increases delivery to the proximal small intestine, the mid-small intestine, the duodenum, the jejunum or the mid-ileum.

In various embodiments, the composition is in the form of a tablet or a capsule.

In various embodiments, the cysteamine salt is cysteamine bitartrate.

Figure 3A:
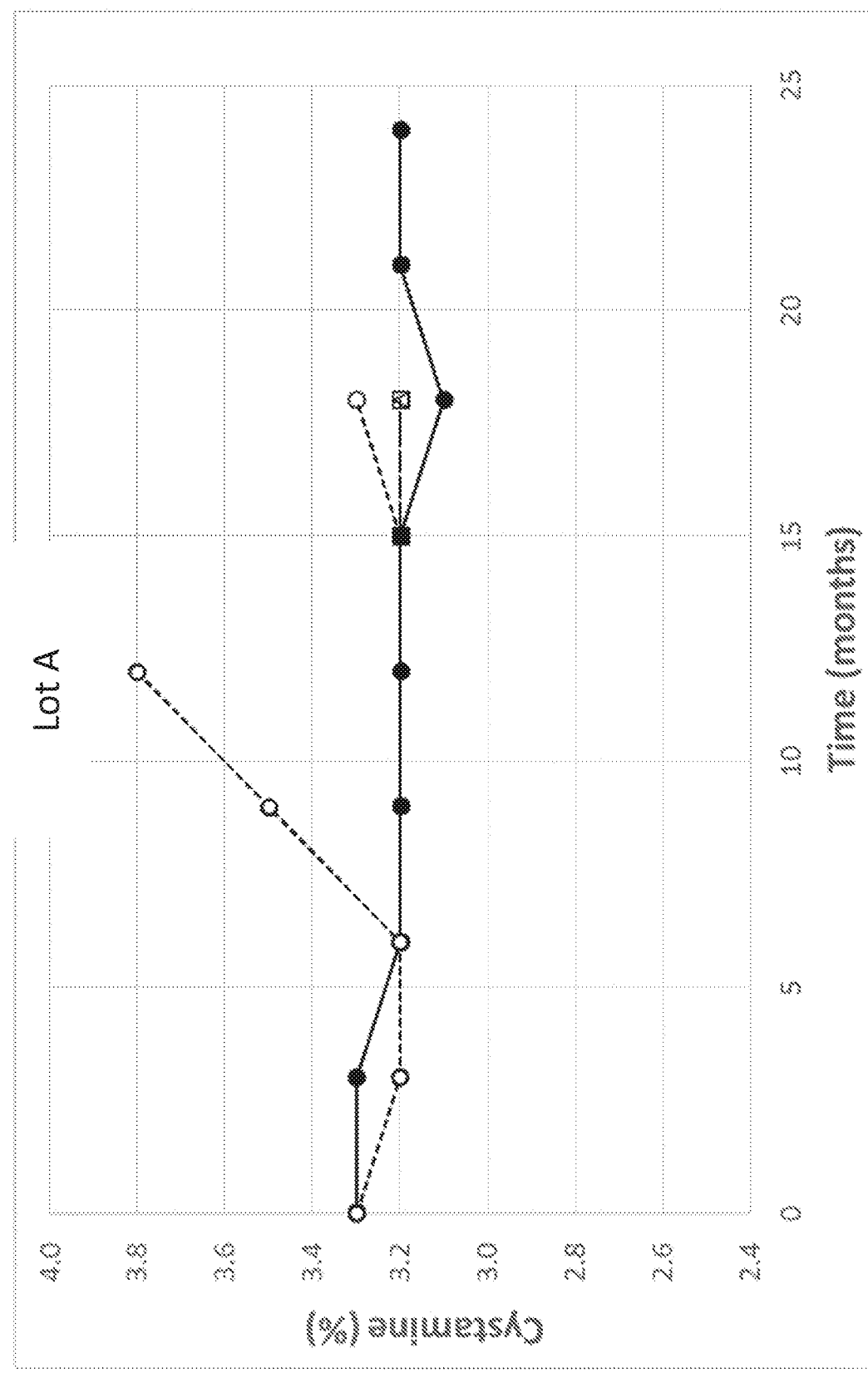
FIG. 3A shows levels of cystamine (relative to cysteamine bitartrate; expressed as a percentage) for samples from Lot A (25-mg PROCYSBI®) after storage at 25° C./60% RH, 30° C./65% RH or 30° C./75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.
Figure 3B:
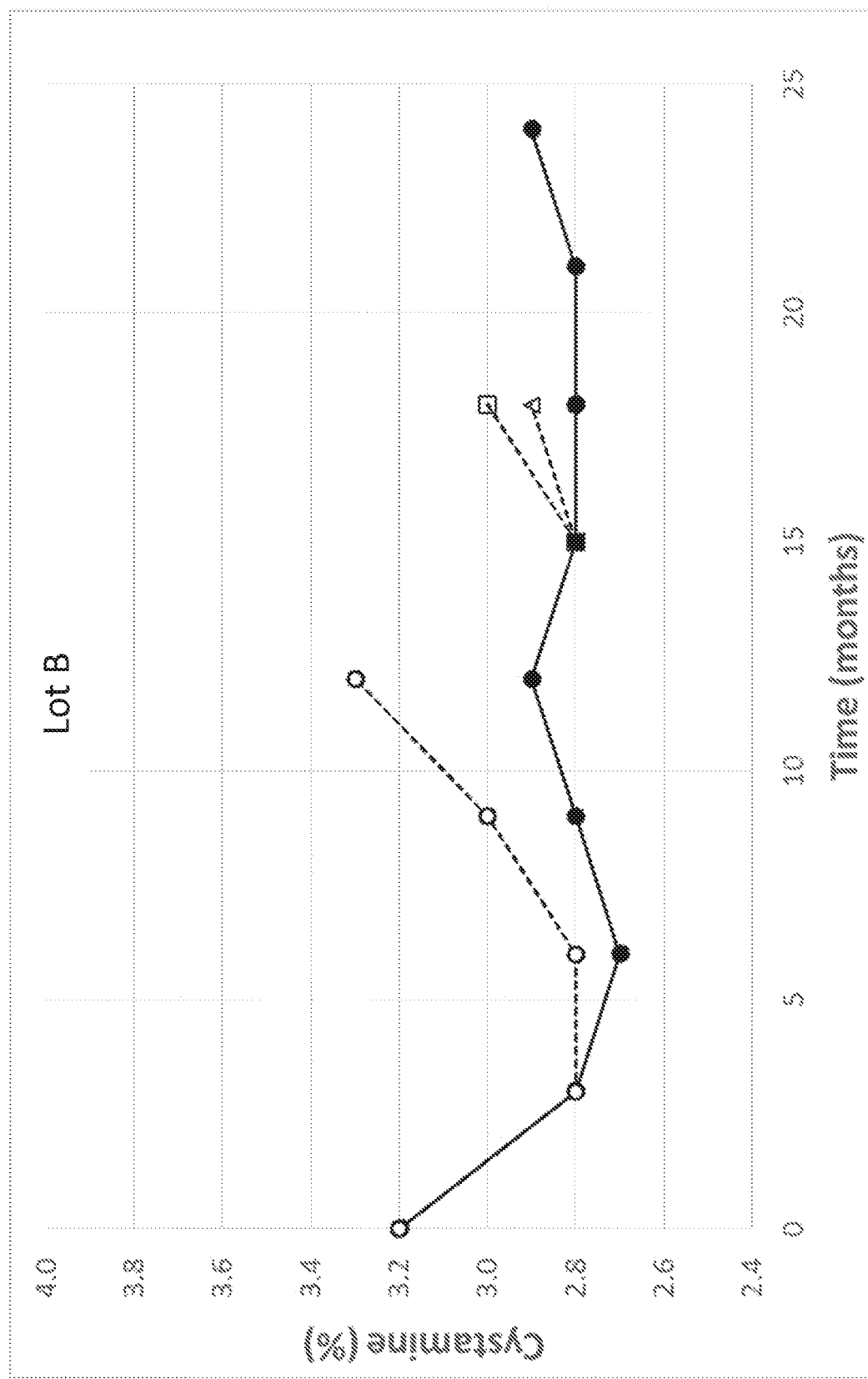
FIG. 3B shows levels of cystamine (relative to cysteamine bitartrate; expressed as a percentage) for samples from Lot B (25-mg PROCYSBI®) after storage at 25° C./60% RH, 30° C./65% RH or 300/75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.
Figure 3C:
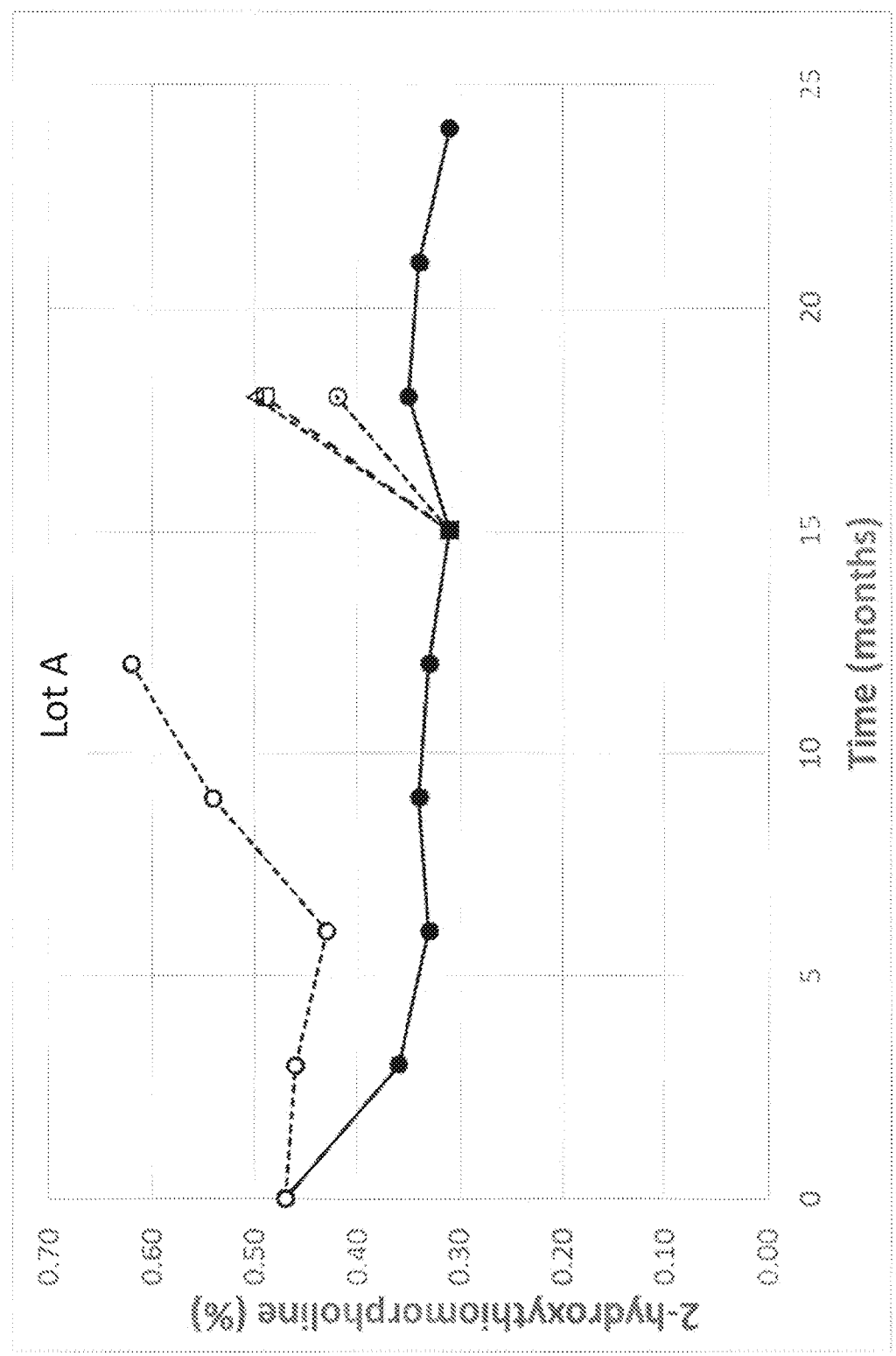

FIG. 3C shows levels of 2-hydroxythiomorpholine (relative to cysteamine bitartrate; expressed as a percentage) for samples form Lot A (25-mg PROCYSBI®) after storage at 25° C./60% RH, 30° C./65% RH or 300/75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.

Figure 3D:
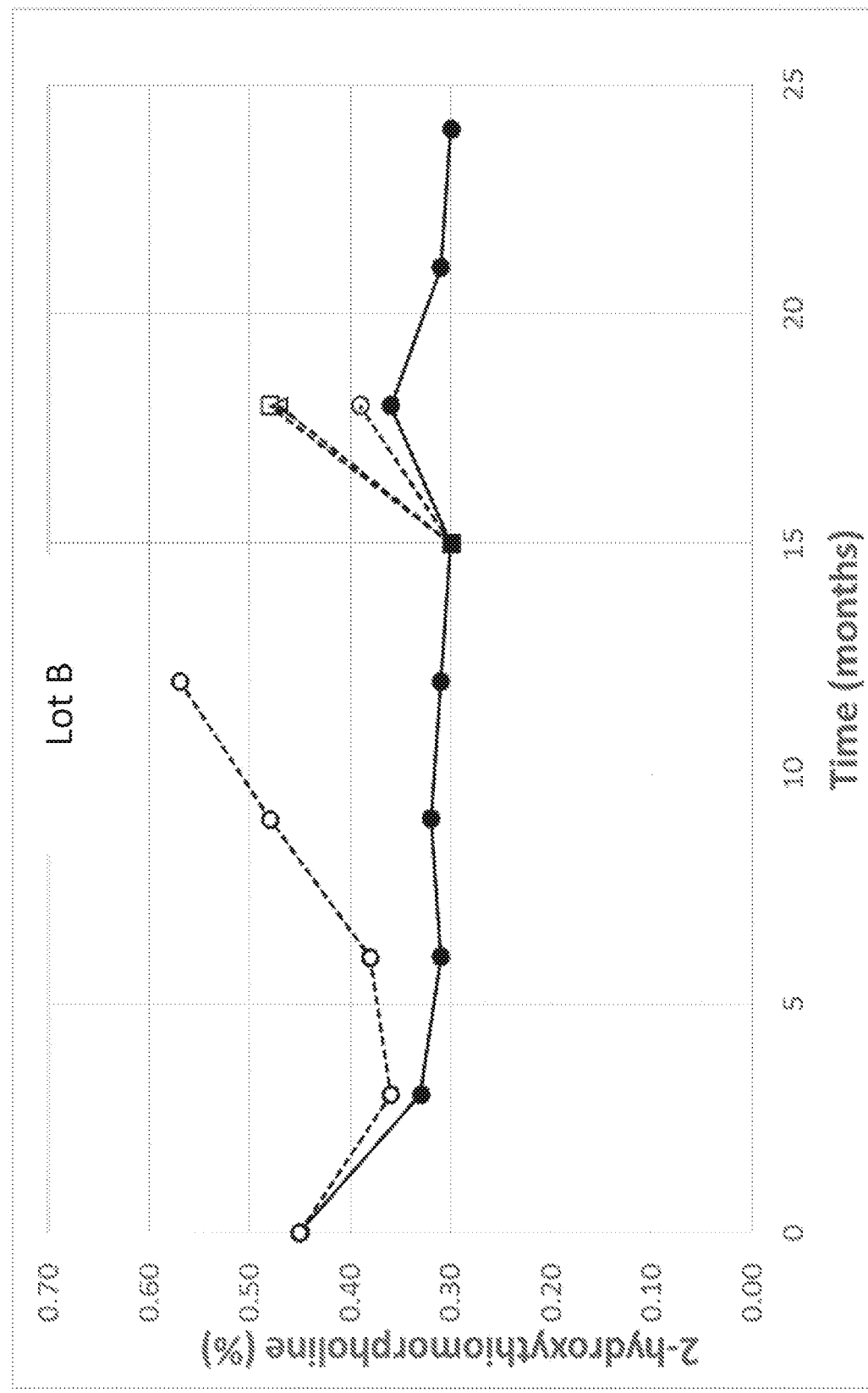

FIG. 3D shows levels of 2-hydroxythiomorpholine (relative to cysteamine bitartrate; expressed as a percentage) for samples from Lot B (25-mg PROCYSBI®) after storage at 25° C./60% RH, 30° C./65% RH or 300/75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.

FIG. 3E shows levels of cystamine tartrate amide (relative to cysteamine bitartrate; expressed as a percentage) for samples from Lot A (25-mg PROCYSBI®) after storage at 25° C./60% RH, 30° C./65% RH or 300/75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.

Figure 3F:
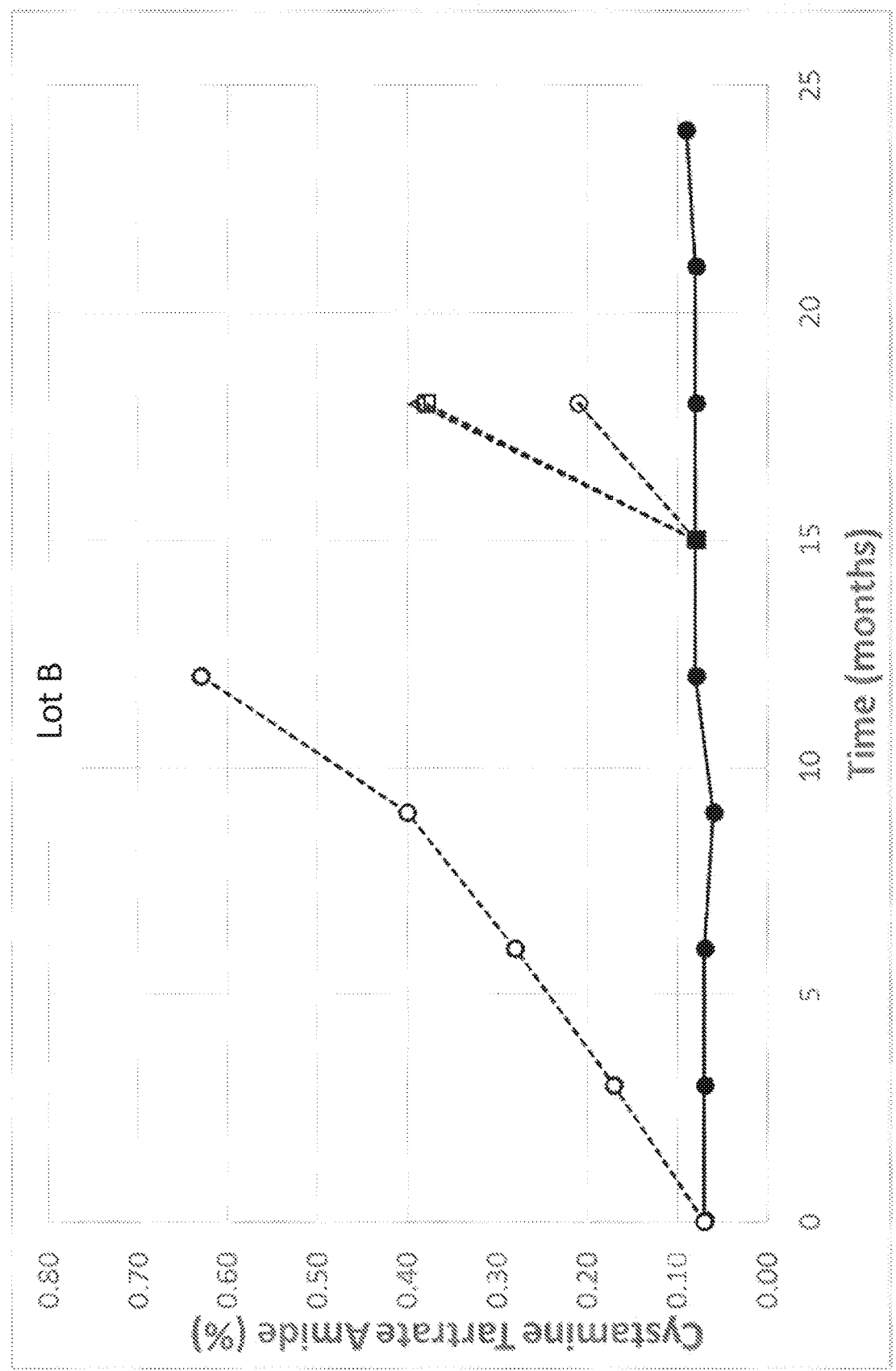

FIG. 3F shows levels of cystamine tartrate amide (relative to cysteamine bitartrate; expressed as a percentage) for samples from Lot B (25-mg PROCYSBI®) after storage at 25° C./60% RH, 30° C./65% RH or 30°/75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.

Figure 3G:
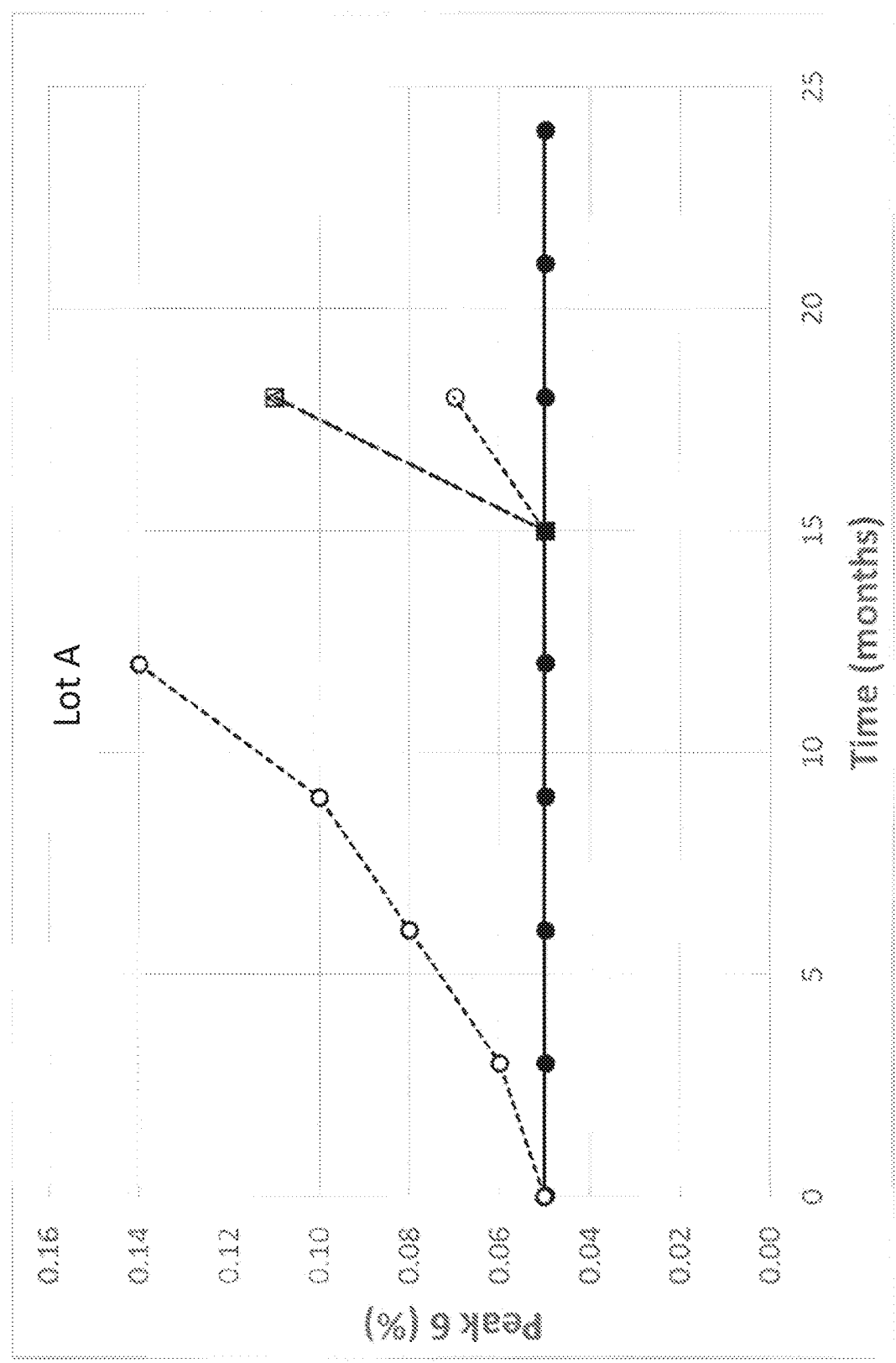

FIG. 3G shows levels of Peak 6 (relative to cysteamine bitartrate; expressed as a percentage) for samples from Lot A (25-mg PROCYSBI®) after storage at 25° C./60% RH, 30° C./65% RH or 300/75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.

Figure 3H:
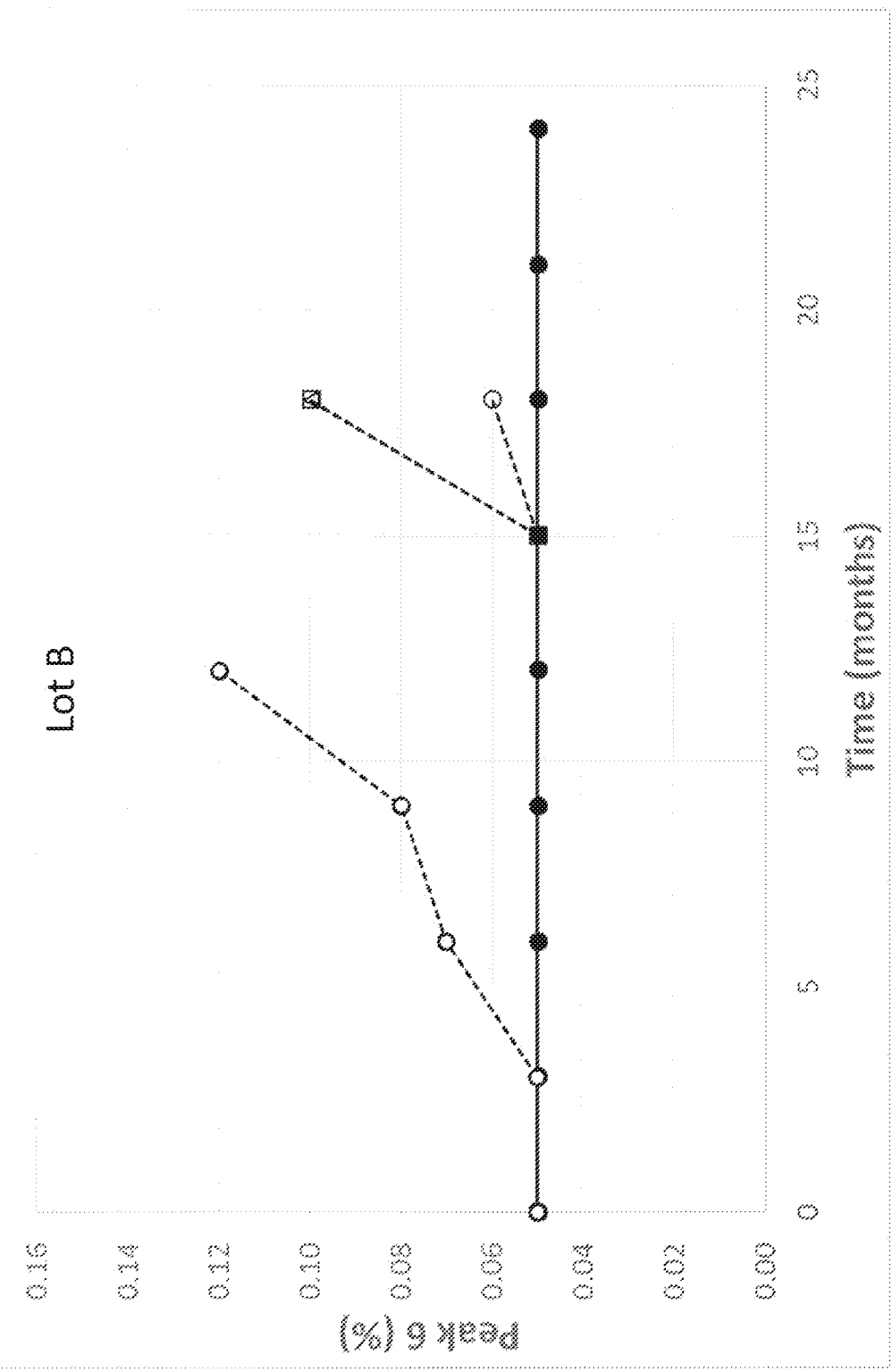

FIG. 3H shows levels of Peak 6 (relative to cysteamine bitartrate; expressed as a percentage) for samples from Lot B (25-mg PROCYSBI®) after storage at 25° C./60% RH, 30° C./65% RH or 30° C./75% RH for 3 months, following 15 months of initial storage at 2° C.-8° C. Closed circles (•) with solid lines represent 2° C.-8° C. data. Open circles (○) with dotted lines represent 25° C./60% RH data for 0-12 month consecutive storage as well as 15-18 months storage at 25° C./60% RH after 15 months storage at 2° C.-8° C. Open squares (□) with dotted lines represent storage at 30° C./65% RH after 15 months storage at 2° C.-8° C. Open triangles (Δ) with dotted lines represent storage at 30° C./75% RH after 15 months storage at 2° C.-8° C.

DETAILED DESCRIPTION

In some aspects, the present disclosure provides methods of storing pharmaceutical compositions comprising cysteamine, or a pharmaceutically acceptable salt thereof, wherein the pharmaceutical composition is stored at refrigerated temperatures (e.g., 2° C.-8° C.) up to 24 months, or longer, and methods for using the same. In particular embodiments, pharmaceutical compositions handled according to the teachings provided herein provide greater chemical stability of cysteamine compared to compositions stored at room temperature. More specifically, the relative amounts of impurities in pharmaceutical compositions handled according to the present disclosure, measured at specific time points, are less than or equal to the corresponding amounts of impurities measured in the compositions when stored at room temperature. Methods for distributing cysteamine compositions are also provided. The present disclosure further provides methods of treating cystinosis comprising administering a pharmaceutical composition comprising cysteamine, or a pharmaceutically acceptable salt thereof, wherein the pharmaceutical composition has been stored under refrigerated temperatures prior to administration.

Definitions

It should be understood that the terms "a" and "an" as used herein refer to "one or more" of the enumerated components. The use of the alternative (e.g., "or") should be understood to mean either one, both, or any combination thereof of the alternatives.

In addition, it should be understood that the individual features, or groups of features, derived from the various combinations of the methods, pharmaceutical compositions, and substituents described herein, are disclosed by the present application to the same extent as if each feature or group of features was set forth individually. Thus, selection of particular features is within the scope of the present disclosure.

As used herein, the terms "include." "have," and "comprise" are used synonymously, which terms and variants thereof are intended to be construed as non-limiting.

The term "consisting essentially of" limits the scope of a claim to the specified materials or steps, or to those that do not materially affect the basic characteristics of a claimed invention.

As used herein, the term "about" means±20% of the indicated range, value, or structure, unless otherwise indicated.

All ranges set forth herein include all possible subsets of ranges and any combinations of such subset ranges. Unless otherwise stated, ranges are inclusive of the stated endpoints. Where a range of values is provided, it is understood that each intervening value between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either or both of those included limits are also contemplated to be part of the disclosure. For example "between 2 and 4" includes, but is not limited to 2, 3, 4, 2 to 3, 3 to 4, and any number falling between 2 and 4.

PROCYSBI® (cysteamine bitartrate; also known as ethanethiol, 2-amino, (2R,3R)-2,3-dihydroxybutanedioate) delayed-release capsules (Raptor Pharmaceuticals, Inc.) is a prescription medicine used for the treatment of nephropathic cystinosis. PROCYSBI® comprises enteric coated cysteamine bitartrate beads encapsulated in gelatin capsules, and currently is available to patients in 25 mg and 75 mg strengths. PROCYSBI® contains the following inactive ingredients: microcrystalline cellulose, Eudragit® L 30 D-55, hypromellose, talc, triethyl citrate, sodium lauryl sulfate, and purified water.

An "enterically coated" drug or tablet refers to a drug, granule, granulation, powder or dosage form, including for example, a tablet, a caplet, and a capsule, that is coated with a substance—i.e., with an "enteric coating"—that remains intact in the stomach but dissolves and releases the drug once the small intestine is reached.

As used herein "enteric coating", is a material, a polymer material or materials which encase the medicament core (e.g., cysteamine, Cystagon®). Typically, a substantial amount or all of the enteric coating material is dissolved before the medicament or therapeutically active agent is released from the dosage form, so as to achieve delayed dissolution of the medicament core. In one embodiment, a suitable pH-sensitive polymer is one which will dissolve in intestinal juices at a higher pH level (pH greater than 4.5), such as within the small intestine and therefore permit release of the pharmacologically active substance in the regions of the small intestine, and not in the upper portion of the GI tract, such as the stomach.

By "pharmaceutically acceptable carrier" or "pharmaceutically acceptable vehicle" are meant materials that are suitable for oral administration and not biologically, or otherwise, undesirable, i.e., that may be administered to a subject along with an active ingredient without causing any undesirable biological effects or interacting in a deleterious manner with any of the other components of a pharmaceutical composition in which it is contained.

Similarly, a "pharmaceutically acceptable" salt, ester, or other derivative of an active agent comprise, for example, salts, esters, or other derivatives which are not biologically or otherwise undesirable.

"Stabilizing agents" refer to compounds that lower the rate at which a pharmaceutical product degrades, particularly an oral pharmaceutical formulation under environmental conditions of storage.

By the terms "effective amount" or "therapeutically effective amount" of a formulation of cysteamine refers to a nontoxic but sufficient amount of the agent to provide the desired therapeutic effect. The exact amount required will vary from subject to subject, depending on the age, weight, and general condition of the subject, the severity of the condition being treated, and the like.

A "solid composition" as used herein refers to any solid-state composition that is, or can be made into, a solid pharmaceutical dosage form. Solid compositions include, for example, bulk powders, granules and granulations (including coated granules), and dosage forms suitable for oral administration to a subject, such as tablets or capsules, including compressed or extruded compositions. Moreover, the term, "solid" does not necessarily imply a complete absence of liquid or gaseous media. For example, solids can have various interstices, which may partially or fully fill with other gaseous and/or liquid media. Thus, the term "solid composition" includes compositions that are suspended (i.e., remain at least partially, if not substantially, insoluble) in liquid media, such as syrups, elixirs, and the like.

"Storage" refers to maintaining a pharmaceutical composition under a set of physical conditions for a period of time. For example, storage can include maintaining a pharmaceutical composition at a particular temperature, humidity, or both (e.g., 25° C./60% RH) for a given duration (e.g., 4 weeks up to 24 months, or longer). As used herein, "storage" can include, for example, storage by a manufacturer, a distributor, a pharmacy, or a hospital prior to dispensing the pharmaceutical composition to a patient or health care provider. "Storage" can also include handling by a patient, wherein the patient maintains a pharmaceutical composition under a set of physical conditions for a period of time.

Addition definitions are set forth throughout this disclosure.

Methods of Storing and Stabilizing Pharmaceutical Compositions

In certain aspects, the present disclosure provides methods of storing or distributing pharmaceutical compositions comprising cysteamine, or a pharmaceutically acceptable salt thereof, wherein the pharmaceutical compositions are stored under refrigerated conditions (e.g., 2° C.-8° C.). When compositions comprising cysteamine are stored at room temperature (e.g., 25° C.), impurities can increase over time as cysteamine degrades. The inventors have found that solid compositions including cysteamine as an active ingredient (or agent) exhibit unexpectedly high levels of impurities associated with cysteamine degradation when stored at 25° C./60% RH for 12 months. Impurities that may increase over time include cystamine, 2-hydroxythiomorpholine, cystamine tartrate amide, 2-hydroxymethylthiazolidine, and Peak 6. In contrast, when cysteamine-containing compositions are stored at temperatures of about 2° C. to about 8° C. for 12 months, or even 24 months, the level of each impurity is less than or equal to that found in the compositions stored at 25° C./60% RH for 12 months.

In one embodiment, the methods as described herein relate to methods involving pharmaceutical compositions comprising cysteamine, or a pharmaceutically acceptable salt thereof, and one or more materials that provide increased delivery of cysteamine to the small intestine. In one embodiment, a material that provides increased delivery of cysteamine to the small intestine comprises an enteric coating. Typically, a substantial amount of all of the enteric coating material is dissolved before the medicament or therapeutically active agent is released from the dosage form, so as to achieve delayed dissolution of the medicament core. For example, a suitable pH-sensitive polymer is one which will dissolve in intestinal juices at a higher pH level (pH greater than 4.5), such as within the small intestine, and therefore permit release of the pharmacologically active substance in the regions of the small intestine and not in the upper portion of the GI tract, such as the stomach. In one embodiment, the enteric material begins to dissolve in an aqueous solution at pH between about 4.5 to about 5.5. In another embodiment, the enteric material begins to dissolve in an aqueous solution at pH between about 5.5 to about 6.5. In another embodiment, the enteric material rapidly dissolves in an aqueous solution at pH between of about 5. In still another embodiment, the enteric material rapidly dissolves in an aqueous solution at pH between of about 5.5. In specific embodiments, the cysteamine-containing composition may be a delayed release solid dosage form containing cysteamine, such as, for example PROCYSBI® (Raptor Pharmaceuticals, Inc.).

For example, pH-sensitive materials will not undergo significant dissolution until the dosage form has emptied from the stomach. The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours (e.g., 2-3 hours) and permit reproducible release therein, the membrane should begin to dissolve within the pH range of the duodenum, and continue to dissolve at the pH range within the small intestine. Therefore, in one embodiment, the amount (thickness) of enteric membrane should be sufficient to be substantially dissolved during the approximate three hour transit time within the small intestine (e.g., the proximal and mid-small intestine).

Enteric (gastro-resistant) materials can include, but are not limited to, one or more of the following: cross-linked polyvinyl pyrrolidone; non-cross linked polyvinylpyrrolidone; hydroxypropylmethyl cellulose phthalate, hydroxypropylmethyl cellulose acetate succinate, cellulose acetate succinate; cellulose acetate phthalate, hydroxypropylmethyl cellulose acetate succinate, cellulose acetate trimellitate; starch acetate phthalate; polyvinyl acetate phthalate; carboxymethyl cellulose; methyl cellulose phthalate; methyl cellulose succinate; methyl cellulose phthalate succinate; methyl cellulose phthalic acid half ester, ethyl cellulose succinate; carboxymethylamide; potassium methacrylated-vinylbenzene copolymer, polyvinylalcohols; polyoxyethyleneglycols; polyethylene glycol; sodium alginate; galactomannone; carboxypolymethylene; sodium carboxymethyl starch; copolymers of acrylic acid and/or methacrylic acid with a monomer selected from the following: methyl methacrylate, ethyl methacrylate, ethyl acrylate, butyl methacrylate, hexyl methacrylate, decyl methacrylate, lauryl methacrylate, phenyl methacrylate, methyl acrylate, isopropyl acrylate, isobutyl acrylate, or octadecyl acrylate, e.g., EUDRAGIT-L and -S series, including L 100-55, L 30 D-55, L 100, S 100, L 12.5, and S 12.5, available from Evonik Industries; polyvinyl acetate; fats; oils; waxes, fatty alcohols; shellac; zein; gluten; ethylacrylate-maleic acid anhydride copolymer, maleic acid anhydride-vinyl methyl ether copolymer; styrol-maleic acid copolymer, 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; polyarginine; poly(ethylene); poly(propylene); poly(ethylene oxide); poly(ethylene terephthalate); poly(vinyl isobutyl ether); poly(vinyl chloride); and polyurethane. A combination of enteric materials may also be used. In one embodiment, the enteric material rapidly dissolves at pH 5.5 and higher, to provide fast dissolution in the upper bowel. For example, the enteric material can be selected from a copolymer of methacrylic acid and methyl methacrylate, and a copolymer of methacrylic acid and ethyl acrylate. For example, an enteric polymer is poly(methacrylic acid co-ethyl acrylate) 1:1 (EUDRAGIT L 30 D-55 and EUDRAGIT L100-55).

Examples of some enteric coatings are disclosed in U.S. Pat. No. 5,225,202, including beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71. April 1984); copolymers of methacrylic acid and methacrylic acid methylester (Eudragits), as a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthalates, e.g., those having a free carboxyl content. See also Remington's Pharmaceutical Sciences, A. Osol, ed., Mack Pub. Co., Easton, Pa. (16$^{th}$ ed. 1980) at pages 1590-1593, and Zeitova et al. (U.S. Pat. No. 4,432,966), for descriptions of suitable enteric coating compositions.

One or more plasticizers can be added to enteric polymers in order to increase their pliability and reduce brittleness, as it is known in the art. Suitable plasticizers are known in the art and include, for example, butyl citrates, triethyl citrate, diethyl phthalate, dibutyl sebacate, PEGs (e.g., PEG 6000), acetyl triethyl citrate, and triacetin. In one type of embodiment, the plasticizer is triethyl citrate. While some enteric materials are flexible and do not require addition of plasticizers, more brittle polymers (e.g., Eudragit US types. Eudragit RL/RS, and Eudragit FS 30 D) benefit from plasticizers, e.g. in the range of 5 wt. % to 30 wt. % based on the dry polymer mass, e.g. about 8 wt. % to about 12 wt. % triethyl citrate with poly(methacrylic acid co-ethyl acrylate) 1:1.

One or more anti-tacking agents (antiadherents) can also be added to an enteric coating mixture in order to reduce the tackiness of the film and prevent agglomeration, as it is known in the art. Anti-tacking agents include talc, and glyceryl monostearate, fumed silica (e.g., AEROSIL 200), precipitated silica (e.g., SIPERNAT PQ), and magnesium stearate, for example. Anti-tacking agents can be used in any suitable quantity, for example in a range of about 10 wt. % to 100 wt. % based on dry polymer mass, or about 10 wt. % to about 50 wt. %, or about 10 wt. % to about 30 wt. %, or about 15 wt. % to about 30 wt. %. For example, in one embodiment the amount of talc is in a range of 15 wt. % to about 30 wt. %, based on dry polymer mass.

One or more surfactants can also be added to an enteric coating mixture in order to improve substrate wettability and/or stabilize suspensions, as it is known in the art. Surfactants include Polysorbate 80, sorbitan monooleate, and sodium dodecyl sulfate, for example.

The enteric membrane can be formed by any suitable process. Coating processes include pan coating, fluid bed coating, and dry coating (e.g., heat dry coating and electrostatic dry coating), for example. Pan coating and fluid bed coating using solvent are well established processes. In liquid coating, the enteric material and optional excipients (e.g., pigments, plasticizers, anti-tacking agents) are mixed in an organic solvent or water to form a solution or dispersion. The coating solution or dispersion is sprayed into solid dosage forms in a pan coater or a fluid bed dryer and dried by hot air. For example, in a Wurster fluid bed coating process, the coating fluid is sprayed from the bottom of the fluid bed apparatus, whereas in an alternative the coating fluid is applied by top spraying, and in another alternative tangential spray is applied.

The amount of enteric material applied is sufficient to achieve desired acid resistance and release characteristics. For example, in one embodiment the amount of enteric membrane will be sufficient to meet United States Pharmacopeia (USP) <711> requirements (USP 36-NF 31) for delayed-release dosage forms, thereby not releasing 10.0 wt. % drug after 2 hours in 0.1N HCl. In another aspect, a formulation will be sufficient to release at least 80% of the active in 20 minutes in pH 6.8 buffer solution, e.g., using the dissolution method of USP 36-NF 31 section <711>.

In one embodiment, an enteric membrane is present in an amount in a range of about 20% to 40%, or 25% to about 35% as measured by the weight gain compared to the uncoated particle cores, or in a range of about 25% to about 31% weight gain, or about 27% to about 31% weight gain, or about 28.5% to about 31% weight gain, based on the weight of the uncoated particle cores.

In pharmaceutical compositions used in the methods described herein, the cysteamine is present in the compositions in a therapeutically effective amount; in one embodiment, the composition is in unit dosage form. The amount of cysteamine administered will be dependent on the age, weight, and general condition of the subject, the severity of the condition being treated, and the judgment of the prescribing physician. In one embodiment, the dose is administered twice per day at about 0.5-1.0 g/m² (e.g., 0.7-0.8 g/m²) body surface area. Current non-enterically coated doses are about 1.35 g/m² body surface area and are administered 4-5 times per day. In another embodiment, the dose is about 0.2-1.95 g/m² body surface area.

In one aspect, a method of storing a pharmaceutical composition is provided, comprising storing the pharmaceutical composition at a temperature of between about 2° C. and about 8° C., wherein the pharmaceutical composition comprises cysteamine, or a pharmaceutically acceptable salt thereof. In another aspect, a method of stabilizing a pharmaceutical composition is provided, comprising storing the pharmaceutical composition at a temperature of between about 2° C. and about 8° C. wherein the pharmaceutical composition comprises cysteamine, or a pharmaceutically acceptable salt thereof.

In any of the aforementioned methods, the pharmaceutical composition may further comprise one or more materials that provide increased delivery of cysteamine to the small intestine. For example, in one embodiment, the material that provides increased delivery of cysteamine to the small intestine comprises an enteric coating, such as a coating selected from the group consisting of polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers formed from methyl acrylate, ethyl acrylate, methyl methacrylate, and/or ethyl methacrylate with copolymers of acrylic and methacrylic acid esters. In one embodiment, the enteric coating comprises poly(methacrylic acid co-ethyl acrylate) 1:1 (Eudragit L 30-D-55).

In any of the aforementioned embodiments, the pharmaceutical composition may comprise a pharmaceutically acceptable salt of cysteamine. In one embodiment, the pharmaceutically acceptable salt of cysteamine is cysteamine bitartrate.

In any of the aforementioned embodiments, the pharmaceutical composition may comprise a solid composition. In one embodiment, the pharmaceutical composition comprises a unit dose of about 25 mg cysteamine. In another embodiment, the pharmaceutical composition comprises a unit dose of about 75 cysteamine. Exemplary pharmaceutical compositions comprising cysteamine are disclosed in International Patent Publication WO 2014/204881.

In various embodiments, the pharmaceutical composition comprises enteric coated beads. In various embodiments, the pharmaceutical composition is a pharmaceutical dosage form that includes a plurality of cysteamine beads, the beads including a core particle including cysteamine or a pharmaceutically acceptable salt thereof and a pharmaceutically acceptable excipient, and an enteric membrane surrounding the core particle, wherein the plurality of beads is characterized by a distribution of particle sizes.

In one embodiment, the particle sizes of the beads are in a range of about 0.7 mm to about 2.5 mm, or about 0.7 mm to about 2.8 mm, or about 0.8 mm to about 1.7 mm. For example, the target bead size can be up to 2.5 mm with no more than 10 percent variation over this size, to a maximum size of 2.8 mm. In one embodiment, the enteric membrane on the beads is present in an amount in a range of about 20% to 40%, or about 20% to about 25%, or about 25% to about 35% as measured by the weight gain compared to the uncoated particle cores, or in a range of about 25% to about 31% weight gain, or about 27% to about 31% weight gain, or about 28.5% to about 31% weight gain, based on the weight of the uncoated particle cores.

In various embodiments, the bead formulation comprises a plurality of cysteamine beads, the beads comprising a core particle comprising cysteamine, optionally cysteamine bitartrate, a filler, a binder and an enteric membrane surrounding the core, wherein the plurality of beads is characterized by a distribution of particle sizes in a range of about 0.7 mm to about 2.8 mm; wherein the enteric membrane is present in an amount in a range of about 20% to about 40% based on the weight of the bead core particles; wherein the formulation is a delayed release formulation having an enteric membrane that begins to dissolve within a pH range of about 4.5 to about 6.5, and wherein the beads are disposed in a capsule shell.

In one embodiment, a method of storing a pharmaceutical composition is provided, comprising storing the pharmaceutical composition at a temperature of between about 2° C. and about 8° C., wherein the pharmaceutical composition comprises cysteamine bitartrate. In a further embodiment, the pharmaceutical composition comprises PROCYSBI®. In another embodiment, a method of stabilizing a pharmaceutical composition is provided, comprising storing the pharmaceutical composition at a temperature of between about 2° C. and about 8° C. wherein the pharmaceutical composition comprises cysteamine bitartrate. In a further embodiment, the pharmaceutical composition comprises PROCYSBI®.

In any of the aforementioned embodiments, the pharmaceutical composition may be stored at a temperature of between about 2° C. and about 8° C. for up to 1 month, between about 1 month and about 6 months, between about 6 months and about 12 months, between about 12 months and about 15 months, between about 15 months and about 18 months, between about 18 months and about 21 months, between about 21 months and about 24 months, between about 24 months and about 36 months, or between about 36 months and about 39 months. In one embodiment, the pharmaceutical composition is stored at a temperature of between about 2° C. and about 8° C. for 1 month, 6 months, 12 months, 15 months, 18 months, 21 months, 24 months, 36 months, or 39 months.

In any of the aforementioned embodiments, the method may further comprise storing the pharmaceutical composition at a temperature of between about 20° C. and about 25° C. and a relative humidity of 60% for up to 4 months.

In any of the aforementioned embodiments, the amount of 2-hydroxythiomorpholine present in the pharmaceutical composition, relative to the amount of cysteamine, or a pharmaceutically acceptable salt thereof, present in the pharmaceutical composition, may be less than 0.5%. For example, in one embodiment, a method of storing a pharmaceutical composition is provided, wherein (a) the pharmaceutical composition is stored at a temperature of between about 2° C. and about 8° C. for up to 24 months. (b) the pharmaceutical composition comprises cysteamine bitartrate, and (c) the amount of 2-hydroxythiomorpholine present in the pharmaceutical composition, relative to the amount of cysteamine bitartrate present in the pharmaceutical composition, is less than 0.5%. In another embodiment, a method of storing or stabilizing a pharmaceutical composition is provided, wherein the amount of 2-hydroxythiomorpholine present in the pharmaceutical composition, relative to the amount of cysteamine, or a pharmaceutically acceptable salt thereof, present in the pharmaceutical composition, is less than or equal to the amount of 2-hydroxythiomorpholine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any one of the aforementioned embodiments, the amount of cystamine present in the pharmaceutical composition, relative to the amount of cysteamine, or a pharmaceutically acceptable salt thereof, present in the pharmaceutical composition, may be less than 4%. For example, in one embodiment, a method of storing a pharmaceutical composition is provided, wherein (a) the pharmaceutical composition is stored at a temperature of between about 2° C. and about 8° C. for up to 24 months, (b) the pharmaceutical composition comprises cysteamine bitartrate, and (c) the amount of cystamine present in the pharmaceutical composition, relative to the amount of cysteamine bitartrate present in the pharmaceutical composition, is less than 4%. In another embodiment, a method of storing or stabilizing a pharmaceutical composition is provided, wherein the amount of cystamine present in the pharmaceutical composition, relative to the amount of cysteamine, or a pharmaceutically acceptable salt thereof, present in the pharmaceutical composition, is less than or equal to the amount of cystamine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of cystamine tartrate amide present in the pharmaceutical composition, relative to the amount of cysteamine, or a pharmaceutically acceptable salt thereof, present in the pharmaceutical composition, may be less than 0.5%. For example, in one embodiment, a method of storing a pharmaceutical composition is provided, wherein (a) the pharmaceutical composition is stored at a temperature of between about 2° C. and about 8° C. for up to 24 months, (b) the pharmaceutical composition comprises cysteamine bitartrate, and (c) the amount of cystamine tartrate amide present in the pharmaceutical composition, relative to the amount of cysteamine bitartrate present in the pharmaceutical composition, is less than 0.5%. In another embodiment, a method of storing or stabilizing a pharmaceutical composition is provided, wherein the amount of cystamine tartrate amide present in the pharmaceutical composition, relative to the amount of cysteamine, or a pharmaceutically acceptable salt thereof, present in the pharmaceutical composition, is less than or equal to the amount of cystamine tartrate amide present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of 2-hydroxymethylthiazolidine present in the pharmaceutical composition, relative to the amount of cysteamine, or a pharmaceutically acceptable salt thereof, present in the pharmaceutical composition, may be less than 0.5%. For example, in one embodiment, a method of storing a pharmaceutical composition is provided, wherein (a) the pharmaceutical composition is stored at a temperature of between about 2° C. and about 8° C. for up to 24 months, (b) the pharmaceutical composition comprises cysteamine bitartrate, and (c) the amount of 2-hydroxymethylthiazolidine present in the pharmaceutical composition, relative to the amount of cysteamine bitartrate present in the pharmaceutical composition, is less than 0.5%. In another embodiment, a method of storing or stabilizing a pharmaceutical composition is provided, wherein the amount of 2-hydroxymethylthiazolidine present in the pharmaceutical composition, relative to the amount of cysteamine, or a pharmaceutically acceptable salt thereof, present in the pharmaceutical composition, is less than or equal to the amount of 2-hydroxymethylthiazolidine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the total amount of 2-hydroxythiomorpholine, cystamine, cystamine tartrate amide, and 2-hydroxymethylthiazolidine present in the pharmaceutical composition, relative to the amount of cysteamine, or a pharmaceutically acceptable salt thereof, present in the pharmaceutical composition, may be less than or equal to the total amount of 2-hydroxythiomorpholine, cystamine, cystamine tartrate amide, and 2-hydroxymethylthiazolidine present in the pharmaceutical composition, relative to the amount cysteamine, or a pharmaceutically acceptable salt thereof, present in the pharmaceutical composition, after storage at a temperature of between about 20° C. and about 25° C. and a relative humidity of 60% for the same duration.

Methods of Distributing Pharmaceutical Compositions

In another aspect, a method of distributing a pharmaceutical composition is provided. In one embodiment, the method comprises storing the pharmaceutical composition at a temperature of between about 2° C. and about 8° C. prior to dispensing to a health care provider or a patient, wherein the pharmaceutical composition comprises cysteamine, or a pharmaceutically acceptable salt thereof. In another embodiment, a pharmaceutical composition comprising cysteamine, or a pharmaceutically acceptable salt thereof, is shipped from a manufacture to a distributor under refrigerated conditions, and is then stored by the distributor prior to dispensing to a health care provider or a patient. In one embodiment, a pharmaceutical composition comprising cysteamine, or a pharmaceutically acceptable salt thereof, is stored by a distributor at a temperature of between about 2° C. and about 8° C. for between about 4 weeks and about 24 months, or longer.

In any of the aforementioned methods of distributing, the pharmaceutical composition may further comprise one or more materials that provide increased delivery of cysteamine to the small intestine. For example, in one embodiment, the material that provides increased delivery of cysteamine to the small intestine comprises an enteric coating, such as a coating selected from the group consisting of polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers formed from methyl acrylate, ethyl acrylate, methyl methacrylate, and/or ethyl methacrylate with copolymers of acrylic and methacrylic acid esters. In one embodiment, the enteric coating comprises poly(methacrylic acid co-ethyl acrylate) 1:1 (Eudragit L 30-D-55).

In any of the aforementioned embodiments, the pharmaceutical composition may comprise a pharmaceutically acceptable salt of cysteamine. In one embodiment, the pharmaceutically acceptable salt of cysteamine is cysteamine bitartrate.

In any of the aforementioned embodiments, the pharmaceutical composition may comprise a solid composition. In one embodiment, the pharmaceutical composition comprises a unit dose of about 25 mg cysteamine. In another embodiment, the pharmaceutical composition comprises a unit dose of about 75 mg cysteamine.

In one embodiment, a method of distributing a pharmaceutical composition is provided, comprising storing the pharmaceutical composition at a temperature of between about 2° C. and about 8° C. prior to dispensing to a health care provider or a patient, wherein the pharmaceutical composition comprises cysteamine bitartrate. In a further embodiment, the pharmaceutical composition comprises PROCYSBI®.

In any of the aforementioned embodiments, the pharmaceutical composition may be stored at a temperature of between about 2° C. and about 8° C. for up to 1 month, between about 1 month and about 6 months, between about 6 months and about 12 months, between about 12 months and about 15 months, between about 15 months and about 18 months, between about 18 months and about 21 months, between about 21 months and about 24 months, between about 24 months and about 36 months, or between about 36 months and about 39 months. In one embodiment, the pharmaceutical composition is stored at a temperature of between about 2° C. and about 8° C. for 1 month, 6 months, 12 months, 15 months, 18 months, 21 months, 24 months, 36 months, or 39 months.

In any of the aforementioned embodiments, the amount of 2-hydroxythiomorpholine present in the pharmaceutical composition, relative to the amount of cysteamine, or a pharmaceutically acceptable salt thereof, present in the pharmaceutical composition, may be less than 0.5%. In another embodiment, a method of distributing a pharmaceutical composition is provided, wherein the amount of 2-hydroxythiomorpholine present in the pharmaceutical composition, relative to the amount of cysteamine, or a pharmaceutically acceptable salt thereof, present in the pharmaceutical composition, is less than or equal to the amount of 2-hydroxythiomorpholine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of cystamine present in the pharmaceutical composition, relative to the amount of cysteamine, or a pharmaceutically acceptable salt thereof, present in the pharmaceutical composition, may be less than 4%. In another embodiment, a method of distributing a pharmaceutical composition is provided, wherein the amount of cystamine present in the pharmaceutical composition, relative to the amount of cysteamine, or a pharmaceutically acceptable salt thereof, present in the pharmaceutical composition, is less than or equal to the amount of cystamine present in the pharmaceutical composition, relative to the amount of cysteamine, or a pharmaceutically acceptable salt thereof, present in the pharmaceutical composition, after storage at a temperature of between about 20° C. and about 25 C° and a relative humidity of 60% for the same duration.

In any of the aforementioned embodiments, the amount of cystamine tartrate amide present in the pharmaceutical composition, relative to the amount of cysteamine, or a pharmaceutically acceptable salt thereof, present in the pharmaceutical composition, may be less than 0.5%. In another embodiment, a method of distributing a pharmaceutical composition is provided, wherein the amount of cystamine tartrate amide present in the pharmaceutical composition, relative to the amount of cysteamine, or a pharmaceutically acceptable salt thereof, present in the pharmaceutical composition, is less than or equal to the amount of cystamine tartrate amide present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of 2-hydroxymethylthiazolidine present in the pharmaceutical composition, relative to the amount of cysteamine, or a pharmaceutically acceptable salt thereof, present in the pharmaceutical composition, may be less than 0.5%. In another embodiment, a method of distributing a pharmaceutical composition is provided, wherein the amount of 2-hydroxymethylthiazolidine present in the pharmaceutical composition, relative to the amount of cysteamine, or a pharmaceutically acceptable salt thereof, present in the pharmaceutical composition, is less than or equal to the amount of 2-hydroxymethylthiazolidine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the total amount of 2-hydroxythiomorpholine, cystamine, cystamine tartrate amide, and 2-hydroxymethylthiazolidine present in the pharmaceutical composition, relative to the amount of cysteamine, or a pharmaceutically acceptable salt thereof, present in the pharmaceutical composition, may be less than or equal to the total amount of 2-hydroxythiomorpholine, cystamine, cystamine tartrate amide, and 2-hydroxymethylthiazolidine present in the pharmaceutical composition, relative to the amount of cysteamine, or a pharmaceutically acceptable salt thereof, present in the pharmaceutical composition, after storage at a temperature of between about 200 and about 25° and a relative humidity of 60% for the same duration.

Method of Treatment

In another aspect, the present disclosure provides methods of treating a disease or disorder by administering to a subject in need thereof a pharmaceutical composition comprising cysteamine, or a pharmaceutically acceptable salt thereof, wherein the pharmaceutical composition has been stored at a temperature of between about 2° C. and about 8° C. prior to administration. In various embodiments, the disease or disorder is cystinosis, fatty liver disease, a thrombotic disease, an MECP-2 related disorder, an inherited mitochondrial disease, a neurological disease or disorder, inflammation and cancer.

In various embodiments, the fatty liver disease is selected from the group consisting of non-alcoholic fatty liver disease (NAFLD), non-alcoholic steatohepatitis (NASH), fatty liver disease resulting from hepatitis, fatty liver disease resulting from obesity, fatty liver disease resulting from diabetes, fatty liver disease resulting from insulin resistance, fatty liver disease resulting from hypertriglyceridemia, Abetalipoproteinemia, glycogen storage diseases. Weber-Christian disease, Wolmans disease, acute fatty liver of pregnancy, and lipodystrophy.

In various embodiments, the thrombotic disease is selected from the group consisting of sickle cell disease, deep vein thrombosis, pulmonary embolism, cardiac embolism, hypercoagulable state, thrombophilia, Factor V Leiden, Antithrombin III deficiency, Protein C deficiency. Protein S deficiency. Prothrombin gene mutation (G20210A), Hyperhomcysteinemia, antiphospholipid antibody syndrome (APS), anticardiolipin antibody (ACLA) thrombosis syndrome, or lupus anticoagulant (LA) syndrome.

In various embodiments, the neurological disease or disorder is selected from the group consisting of Huntington's Disease, Parkinson's Disease, amyotrophic lateral sclerosis, multiple sclerosis. Alzheimer's disease spinal muscle atrophy, concussion, stroke, and traumatic brain injury (TBI).

In various embodiments, the MECP-2 related disease is selected from the group consisting of Rett syndrome, autism, pervasive development disorder, non-syndromic mental retardation, idiopathic neonatal encephalopathy and idiopathic cerebral palsy.

In various embodiments, the inherited mitochondrial disease is selected from the group consisting of Friedreich's ataxia, Leber's hereditary optic neuropathy (LHON), myo-clonic epilepsy and ragged-red fibers, mitochondrial encephalomyopathy, lactic acidosis, and stroke-like syndrome (MELAS). Keam-Sayre syndrome and subacute necrotizing encephalopathy (Leigh's Syndrome).

In various embodiments, the cancer is selected from the group consisting of breast cancer, melanoma, prostate cancer, pancreatic cancer, head and neck cancer, lung cancer, non small-cell lung carcinoma, renal cancer, colorectal cancer, colon cancer, ovarian cancer, liver cancer and gastric cancer.

In one aspect, the cysteamine composition is administered in dosage form, wherein the dose is administered either one time per day or multiple times per day. The cysteamine composition may be administered less than four times per day, e.g., one, two or three times per day. In some embodiments, an effective dosage of cysteamine composition may be within the range of 0.01 mg to 1000 mg per kg (mg/kg) of body weight per day. Further, the effective dose may be 0.5 mg/kg, 1 mg/kg, 5 mg/kg, 10 mg/kg, 15 mg/kg, 20 mg/kg/25 mg/kg, 30 mg/kg, 35 mg/kg, 40 mg/kg, 45 mg/kg, 50 mg/kg, 55 mg/kg, 60 mg/kg, 70 mg/kg, 75 mg/kg, 80 mg/kg, 90 mg/kg, 100 mg/kg, 125 mg/kg, 150 mg/kg, 175 mg/kg, 200 mg/kg, 225 mg/kg, 250 mg/kg, 275 mg/kg, 300 mg/kg, 325 mg/kg, 350 mg/kg, 375 mg/kg, 400 mg/kg, 425 mg/kg, 450 mg/kg, 475 mg/kg, 500 mg/kg, 525 mg/kg, 550 mg/kg, 575 mg/kg, 600 mg/kg, 625 mg/kg, 650 mg/kg, 675 mg/kg, 700 mg/kg, 725 mg/kg, 750 mg/kg, 775 mg/kg, 800 mg/kg, 825 mg/kg, 850 mg/kg, 875 mg/kg, 900 mg/kg, 925 mg/kg, 950 mg/kg, 975 mg/kg or 1000 mg/kg, or may range between any two of the foregoing values. In some embodiments, the dose above may be the total daily dose, or may be the dose administered in one of the one, two or three daily administrations. In some embodiments, the cysteamine composition is administered at a total daily dose of from approximately 0.25 g/m2 to 4.0 g/m2 body surface area, e.g., at least about 0.5, 0.6, 0.7, 0.8, 0.9, 1.0, 1.1, 1.2, 1.3, 1.4, 1.5, 1.6, 1.7, 1.8, 1.9 or 2 g/m2, or up to about 0.8, 0.9, 1.0, 1.1, 1.2, 1.3, 1.4, 1.5, 1.6, 1.7, 1.8, 1.9, 2.0, 2.2, 2.5, 2.7, 3.0, or 3.5 g/m2 or may range between any two of the foregoing values. In some embodiments, the cysteamine composition may be administered at a total daily dose of about 0.5-2.0 $g/m^2$ body surface area, or 1-1.5 $g/m^2$ body surface area, or 0.5-1 $g/m^2$ body surface area, or about 0.7-0.8 $g/m^2$ body surface area, or about 1.3 $g/m^2$ body surface area (e.g., about 1.35 $g/m^2$ body surface area), or about 1.3 to about 1.95 $grams/m^2/day$, or about 0.5 to about 1.5 $grams/m^2/day$, or about 0.5 to about 1.0 $grams/m^2/day$, preferably at a frequency of fewer than four times per day, e.g. three, two or one times per day. Salts or esters of the same active ingredient may vary in molecular weight depending on the type and weight of the salt or ester moiety. For administration of enteric dosage form, e.g., a tablet or capsule or other oral dosage form comprising the enterically coated cysteamine product, a total weight in the range of approximately 100 mg to 1000 mg is used. In certain embodiments, the amount of cysteamine active ingredient in a tablet or capsule is approximately 15, 20, 25, 50, 75, 100, 125, 150, 175, 200, 250, 300, 400 or 500 mg.

In one embodiment, provided is a method of treating cystinosis, comprising administering a therapeutically effective amount of a pharmaceutical composition comprising cysteamine, or a pharmaceutically acceptable salt thereof, wherein the pharmaceutical composition has been stored at a temperature of between about 2° C. and about 8° C. prior to administration.

In various embodiments, the pharmaceutical composition is formulated to provide white blood cell cystine suppression with a 12 hour level below 1 nmol ½ cystine/mg protein.

In various embodiments, each dose of cysteamine is about 0.5-1.0 g/m2 body surface area. In various embodiments, the total daily dose of cysteamine is about 1.30 g/m2 body surface area or less.

In various embodiments, the composition increases delivery to the proximal small intestine, the mid-small intestine, the duodenum, the jejunum or the mid-ileum.

In various embodiments, the composition is in the form of a tablet or a capsule.

In various embodiments, the cysteamine salt is cysteamine bitartrate.

The methods of treatment of the disclosure can be used in combination with other therapies useful for treating cystinosis and neurodegenerative diseases and disorders. For example, indomethacin therapy (Indocid® or Endol®) is an anti-inflammatory used to treat rheumatoid arthritis and lumbago, but it can be used to reduce water and electrolyte urine loss. In children with cystinosis, indomethacin reduces the urine volume and therefore liquid consumption by about 30%, sometimes by half. In most cases this is associated with an appetite improvement. Indomethacin treatment is generally followed for several years.

Other therapies can be combined with the methods and compositions of the disclosure to treat diseases and disorders that are attributed to or result from cystinosis. Urinary phosphorus loss, for example, entails rickets, and it may be necessary to give a phosphorus supplement. Carnitine is lost in the urine and blood levels are low. Carnitine allows fat to be used by the muscles to provide energy. Hormone supplementation is sometimes necessary. Sometimes the thyroid gland will not produce enough thyroid hormones. This is given as thyroxin (drops or tables). Insulin treatment is sometimes necessary if diabetes appears, when the pancreas does not produce enough insulin. These treatments have become rarely necessary in children whom are treated with cysteamine, since the treatment protects the thyroid and the pancreas. Some adolescent boys require a testosterone treatment if puberty is late. Growth hormone therapy may be indicated if growth is not sufficient despite a good hydro electrolytes balance. Accordingly, such therapies can be combined with the enterically coated cysteamine and cystamine compositions and methods of the disclosure.

The effectiveness of a method of the disclosure can be assessed by measuring leukocyte cystine concentrations. Dosage adjustment and therapy can be made by a medical specialist depending upon, for example, the severity of cystinosis and/or the concentration of cystine. Additional therapies including the use of omeprazole (Prilosec®) can reduce these symptoms.

Accordingly, in one embodiment, the present disclosure provides a method of treating cystinosis, comprising administering a pharmaceutical composition comprising cysteamine, or a pharmaceutically acceptable salt thereof, wherein the pharmaceutical composition has been stored at a temperature of between about 2° C. and about 8° C. prior to administration. In another embodiment, a method of treating cystinosis is provided, wherein the pharmaceutical composition has been first stored at a temperature of between about 2° C. and about 8° C. prior to administration and is subsequently stored at a temperature of between about 20° C. and about 25° C. and a relative humidity of 60% for up to 4 months prior to administration.

In any of the aforementioned methods of treatment, the pharmaceutical composition may further comprise one or more materials that provide increased delivery of cysteamine to the small intestine. For example, in one embodiment, the material that provides increased delivery of cysteamine to the small intestine comprises an enteric coating, such as a coating selected from the group consisting of polymerized gelatin, shellac, methacrylic acid copolymer type CNF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers formed from methyl acrylate, ethyl acrylate, methyl methacrylate, and/or ethyl methacrylate with copolymers of acrylic and methacrylic acid esters. In one embodiment, the enteric coating comprises poly(mcthacrylic acid co-ethyl acrylate) 1:1 (Eudragit L 30-D-55).

In any of the aforementioned embodiments, the pharmaceutical composition may comprise a pharmaceutically acceptable salt of cysteamine. In one embodiment, the pharmaceutically acceptable salt of cysteamine is cysteamine bitartrate.

In any of the aforementioned embodiments, the pharmaceutical composition may comprise a solid composition. In one embodiment, the pharmaceutical composition comprises a unit dose of about 25 mg cysteamine. In another embodiment, the pharmaceutical composition comprises a unit dose of about 75 mg cysteamine. In various embodiments, the pharmaceutical composition is a bead formulation as described herein.

In one embodiment, a method of treating cystinosis is provided, comprising administering a pharmaceutical composition comprising cysteamine bitartrate, wherein the pharmaceutical composition has been stored at a temperature of between about 2° C. and about 8° C. prior to administration. In another embodiment, a method of treating cystinosis is provided, comprising administering a pharmaceutical composition comprising cysteamine bitartrate, wherein the pharmaceutical composition has been first stored at a temperature of between about 2° C. and about 8° C. prior to administration and subsequently stored at a temperature of between about 20° C. and about 25° C. and a relative humidity of 60% for up to 4 months prior to administration. In further embodiment, the pharmaceutical composition comprises PROCYSBI®.

In any of the aforementioned embodiments, the pharmaceutical composition may be stored at a temperature of between 2° C. and about 8° C. for up to 1 month, between about 1 month and about 6 months, between about 6 months and about 12 months, between about 12 months and about 15 months, between about 15 months and about 18 months, between about 18 months and about 21 months, between about 21 months and about 24 months, between about 24 months and about 36 months, or between about 36 months and about 39 months. In one embodiment, the pharmaceutical composition is stored at a temperature of between about 2° C. and about 8° C. for 1 month, 6 months, 12 months, 15 months, 18 months, 21 months, 24 months, 36 months, or 39 months.

In any of the aforementioned embodiments, the amount of 2-hydroxythiomorpholine present in the pharmaceutical composition, relative to the amount of cysteamine, or a pharmaceutically acceptable salt thereof, present in the pharmaceutical composition, may be less than 0.5%. In another embodiment, a method of treating a cystinosis is provided, wherein the amount of 2-hydroxythiomorpholine present in the pharmaceutical composition, relative to the amount of cysteamine, or a pharmaceutically acceptable salt thereof, present in the pharmaceutical composition, is less than or equal to the amount of 2-hydroxythiomorpholine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of cystamine present in the pharmaceutical composition, relative to the amount of cysteamine, or a pharmaceutically acceptable salt thereof, present in the pharmaceutical composition, may be less than 4%. In another embodiment, a method of treating cystinosis is provided, wherein the amount of cystamine present in the pharmaceutical composition, relative to the amount of cysteamine, or a pharmaceutically acceptable salt thereof, present in the pharmaceutical composition, is less than or equal to the amount of cystamine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of cystamine tartrate amide present in the pharmaceutical composition, relative to the amount of cysteamine, or a pharmaceutically acceptable salt thereof, present in the pharmaceutical composition, may be less than 0.5%. In another embodiment, a method of treating cystinosis is provided, wherein the amount of cystamine tartrate amide present in the pharmaceutical composition, relative to the amount of cysteamine, or a pharmaceutically acceptable salt thereof, present in the pharmaceutical composition, is less than or equal to the amount of cystamine tartrate amide present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the amount of 2-hydroxymethylthiazolidine present in the pharmaceutical composition, relative to the amount of cysteamine, or a pharmaceutically acceptable salt thereof, present in the pharmaceutical composition, may be less than 0.5%. In another embodiment, a method of treating cystinosis is provided, wherein the amount of 2-hydroxymethylthiazolidine present in the pharmaceutical composition, relative to the amount of cysteamine, or a pharmaceutically acceptable salt thereof, present in the pharmaceutical composition, is less than or equal to the amount of 2-hydroxymethylthiazolidine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the total amount of 2-hydroxythiomorpholine cystamine, cystamine tartrate amide, and 2-hydroxymethylthiazolidine present in the pharmaceutical composition, relative to the amount of cysteamine, or a pharmaceutically acceptable salt thereof, present in the pharmaceutical composition, may be less than or equal to the total amount of 2-hydroxythiomorpholine, cystamine, cystamine tartrate amide, and 2-hydroxymethylthiazolidine present in the pharmaceutical composition, relative to the amount of cysteamine, or a pharmaceutically acceptable salt thereof, present in the pharmaceutical composition, after storage at a temperature of between about 20° C. and about 25° C. and a relative humidity of 60% for the same duration.

In any of the aforementioned embodiments, the cystinosis may be nephropathic cystinosis.

In another aspect, the present disclosure provides methods of treating a disease or disorder, comprising administering a therapeutically effective amount of a pharmaceutical composition comprising cysteamine, or a pharmaceutical acceptable salt thereof, wherein the pharmaceutical composition has been stored at a temperature of between about 2° C. and about 8° C. prior to administration. In another embodiment, a method of treating a disease or disorder is provided, wherein the pharmaceutical composition has been first stored at a temperature of between about 2° C. and about 8° C. prior to administration and is subsequently stored at a temperature of between about 20° C. and about 25° C. and a relative humidity of 60% for up to 4 months prior to administration. In various embodiments, the disease or disorder is cystinosis, fatty liver disease, a thrombotic disease, an MECP-2 related disorder, an inherited mitochondrial disease, a neurological disease or disorder, inflammation and cancer. In one embodiment, the disease or disorder is a metabolic and neurodegenerative disease, such as non-alcoholic fatty liver disease (NAFLD), non-alcoholic steatohepatitis (NASH), Huntington's disease, Parkinson's disease, Rett Syndrome, or cystic fibrosis. In another embodiment, the disease or disorder is a fibrotic disorder or an inflammatory disorder.

EXAMPLES

Example 1

Impurity Levels in PROCYSBI® after Storage at 25° C.

Nineteen impurities have been identified for PROCYSBI® (Table 1). Seven of these impurities do not increase during storage at 25° C./60% relative humidity (RH): Peak 3, Peak E. RRT 1.41-1.47, Peak F. Peak G, Peak H, and Peak I. Twelve impurities may increase when stored at 25° C./60% RH: cystamine, Peak A. Peak B. Peak C, 2-hydroxythiomorpholine. Peak D, cystamine tartrate amide, 2-hydroxymethylthiazolidine. Peak 5. Peak 6. Peak J, and Peak K.

TABLE 1

Impurities That Do and Do Not Increase on Stability When Stored at 25° C./60% RH

| Impurities that do not increase when stored at 25° C./60% RH | Impurities that may increase when stored at 25° C./60% RH |
|---|---|
| Peak 3 | Cystamine |
| Peak E | Peak A |
| RRT 1.41-1.47 | Peak B |
| Peak F | Peak C |
| Peak G | 2-hydroxythiomorpholine |
| Peak H | Peak D |
| Peak I | Cystamine tartrate amide |
| | 2-hydroxymethylthiazolidine |
| | Peak 5 |
| | Peak 6 |
| | Peak J |
| | Peak K |

Example 2

Storage at 2° C.-8° C. Reduces the Rate of Growth of Impurities in PROCYSBI®

Samples of PROCYSBI® were tested for chemical stability after storage under conditions of either 2° C.-8° C. (refrigerated)/ambient humidity, or 25° C./60% RH (room temperature), for up to 24 months. Samples were placed in controlled environmental chambers, which were maintained at the described temperature (±2° C.) and relative humidity (±5%). At each scheduled time point, samples were removed from each storage condition within 1 week of the scheduled date, and held at ambient conditions until analyzed. Amounts of cysteamine bitartrate and the 12 impurities that may grow on stability at 25° C./60% RH (cystamine, Peak A, Peak B, Peak C, 2-hydroxythiomorpholine, Peak D, cystamine tartrate amide, 2-hydroxymethylthiazolidine, Peak 5, Peak 6. Peak J, and Peak K), as well as total related substances (TRS), were measured by HPLC (gradient pump; waters column; dimensions: 150-mm×4.6-mm (i.d.); Xbridge C1s packing, 3.5-μm particle size; detection: UV @ 210 nm; Injection Volume: 10 μL for assay, 100 μL for related substance (RS) testing; flow rate: 1.0 mL/min; column temperature: 40° C.; autosampler temperature: 4° C.; run time 40 minutes). The mobile phases were 23.6 mM 1-octanesulfonic acid sodium and 29.0 mM sodium phosphate pH 2.6/ACN/MeOH 85/3/12 (v/v/v) (mobile phase A) and 0.20 M 1-octanesulfonic acid sodium and 0.10 M sodium phosphate pH 2.6/ACN/MeOH 10/18/72 (v/v/v) (mobile phase B). Elution was performed using a gradient (linear) under the following parameters:

| Time (min.) | % A | % B |
|---|---|---|
| 0.0 | 100 | 0 |
| 2.0 | 100 | 0 |
| 20.0 | 60 | 40 |
| 25.0 | 60 | 40 |
| 25.1 | 100 | 0 |
| 40.0 | 100 | 0 |

The limit of quantitation (LOQ) was 0.05%. For graphical purposes, values at or below LOQ are presented at 0.05%. Data for the amount of cysteamine bitartrate in the samples are calculated relative to the label claim of 25 mg or 75 mg ("Assay"). Acid dissolution and buffer dissolution tests were conducted in accordance with the dissolution method of USP 36-NF 31 section <711>. In brief, in the acid dissolution test, the composition was mixed with 0.1M HCl for 2 hours, at which time a sample of the fluid was taken and assayed for the amount of cysteamine bitartrate present. In the buffer dissolution test, the composition was immediately transferred from the acid solution to a pH 6.8 buffer solution, and the liquid was sampled after either 20 minutes or 30 minutes. Graphical representation (e.g., the Y-axes) of acid dissolution and buffer dissolution data are shown relative to the label claim of 25 mg or 75 mg. Graphical (e.g., the Y-axes) and tabular representation of impurities data show the amount of a given chemical impurity relative to the amount of cysteamine bitartrate measured in that chromatogram (i.e., the ratio of the amount of the impurity to the amount of cysteamine bitartrate, expressed as a percent). Graphical and tabular representations of time in months were also rounded to the nearest integer.

Figure 1A:
FIG. 1A shows a comparison of cold storage (2° C. to 8° C.) to room temperature storage (25° C./60% RH) for the amount of cysteamine bitartrate (relative the label claim; expressed as a percent) in samples of 25-mg PROCYSBI® ("Assay"). Open circles and squares (○, □) with dotted lines represent 25° C./60% RH data for lots A and B, respectively. Closed circles and squares (•, ■) with solid lines represent 2° C.-8° C. data for lots A and B, respectively.
Figure 1B:
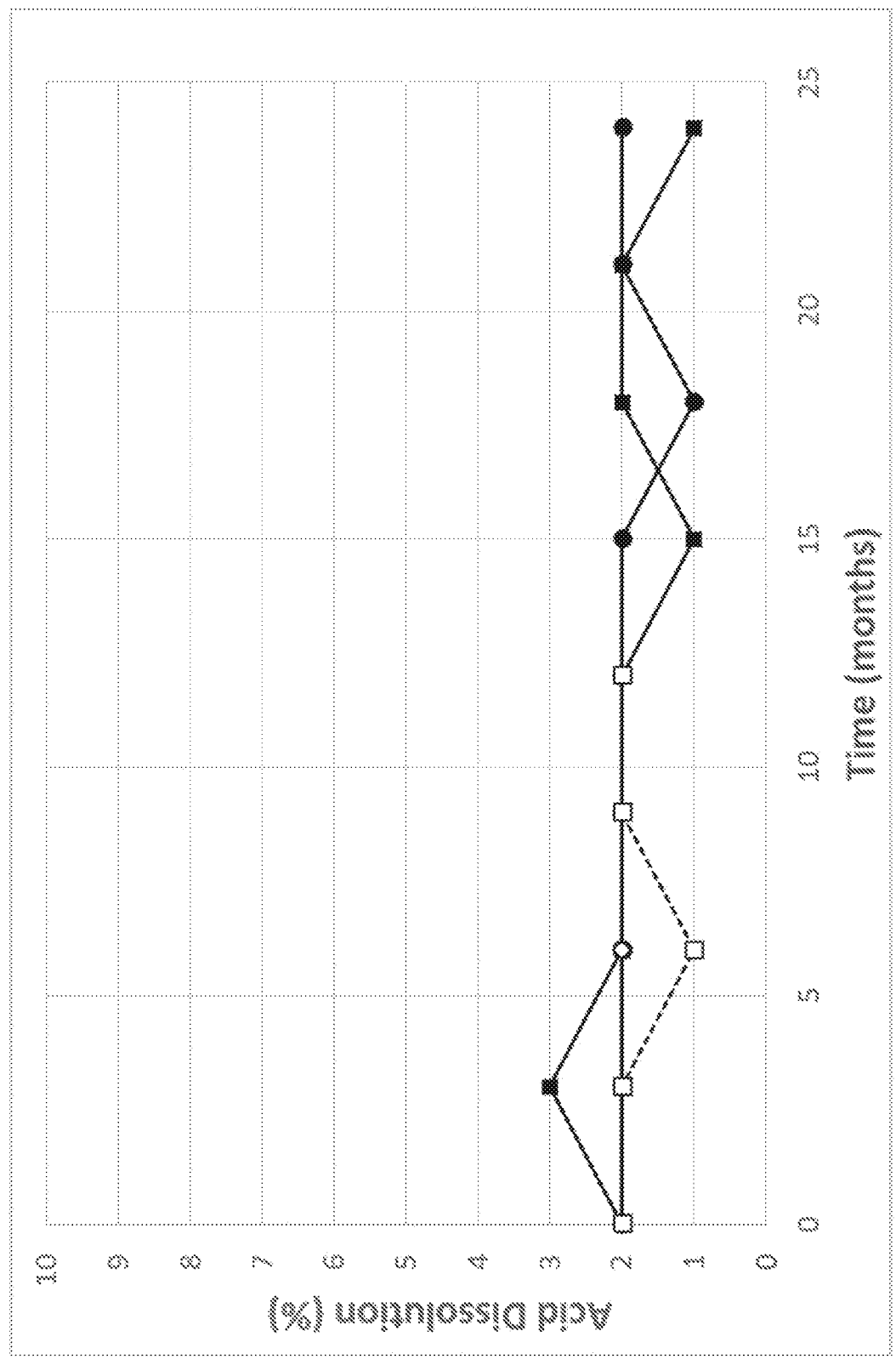
FIG. 1B shows a comparison of cold storage (2° C.-8° C.) to room temperature storage (25° C./60% RH) for acid stage dissolution tests of samples of 25-mg PROCYSBI® (relative the label claim; expressed as a percent). Open circles and squares (○, □) with dotted lines represent 25° C./60% RH data for lots A and B, respectively. Closed circles and squares (•, ■) with solid lines represent 2° C.-8° C. data for lots A and B, respectively.
Figure 1C:
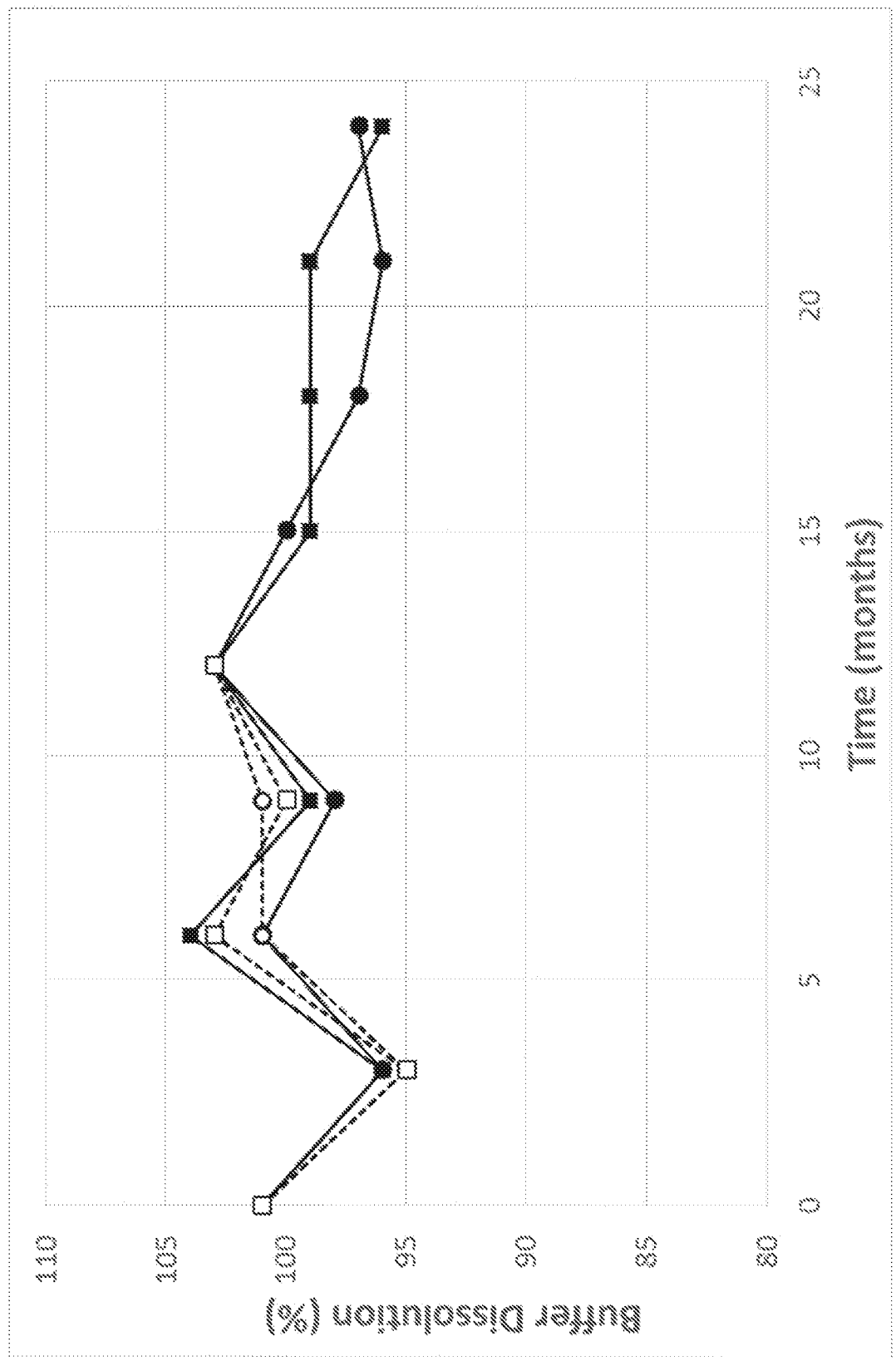
FIG. 1C shows a comparison of cold storage (2° C.-8° C.) to room temperature storage (25° C./60% RH) for buffer stage dissolution tests of samples of 25-mg PROCYSBI® (relative the label claim; expressed as a percent). Open circles and squares (○, □) with dotted lines represent 25° C./60% RH data for lots A and B, respectively. Closed circles and squares (•, ■) with solid lines represent 2° C.-8° C. data for lots A and B, respectively.
Figure 1D:
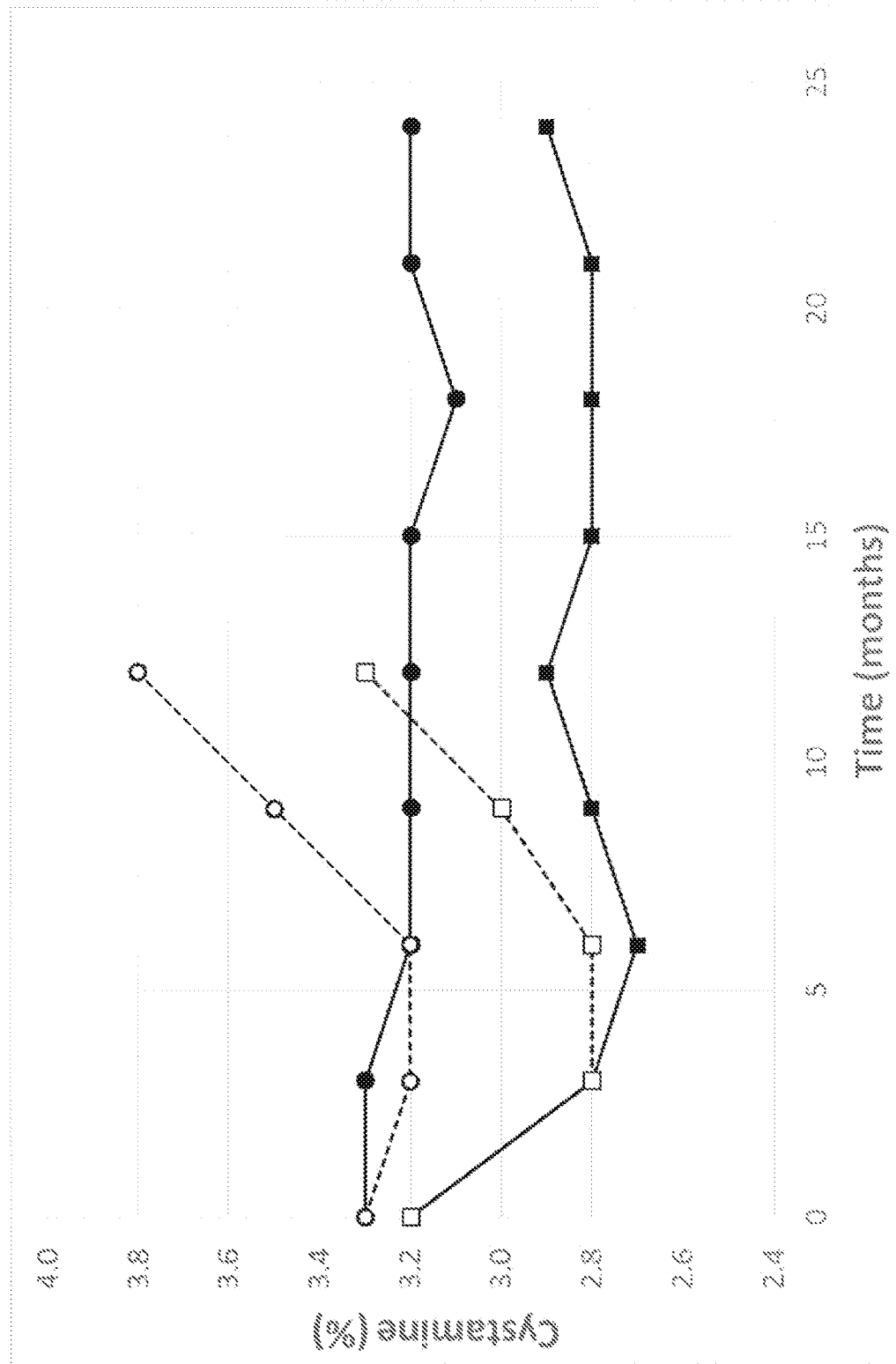
FIG. 1D shows comparisons of cold storage (2° C.-8° C.) to room temperature storage (25° C./60% RH) for cystamine (relative to cysteamine bitartrate; expressed as a percentage) in samples of 25-mg PROCYSBI®. Open circles and squares (○, □) with dotted lines represent 25° C./60% RH data for lots A and B, respectively. Closed circles and squares (•, ■) with solid lines represent 2° C.-8° C. data for lots A and B, respectively.
Figure 1E:
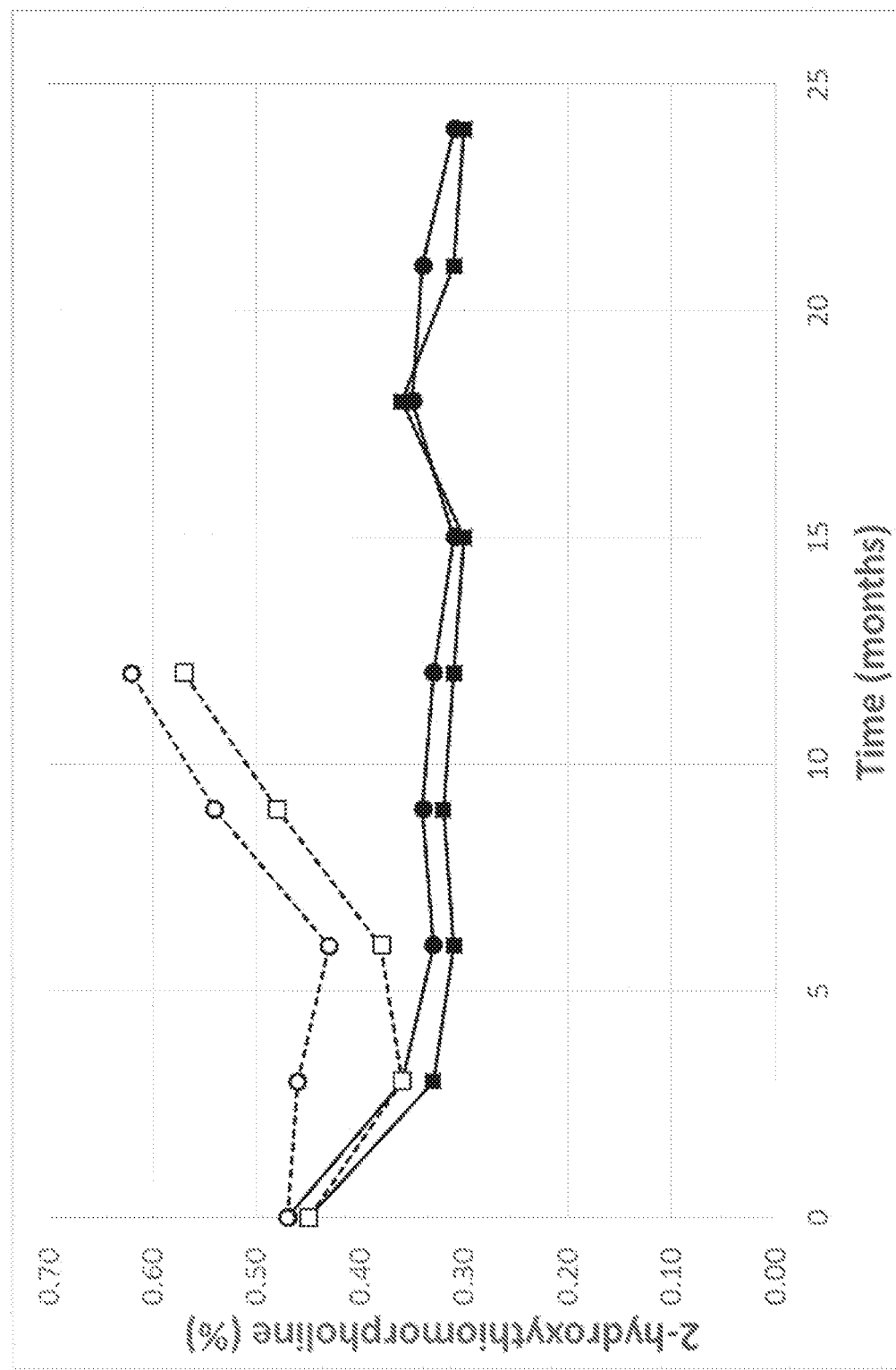
FIG. 1E shows a comparison of cold storage (2° C.-8° C.) to room temperature storage (25° C./60% RH) for 2-hydroxythiomorpholine (relative to cysteamine bitartrate; expressed as a percentage) in samples of 25-mg PROCYSBI®. Open circles and squares (○, □) with dotted lines represent 25° C./60% RH data for lots A and B, respectively. Closed circles and squares (•, ■) with solid lines represent 2° C.-8° C. data for lots A and B, respectively.
Figure 1F:
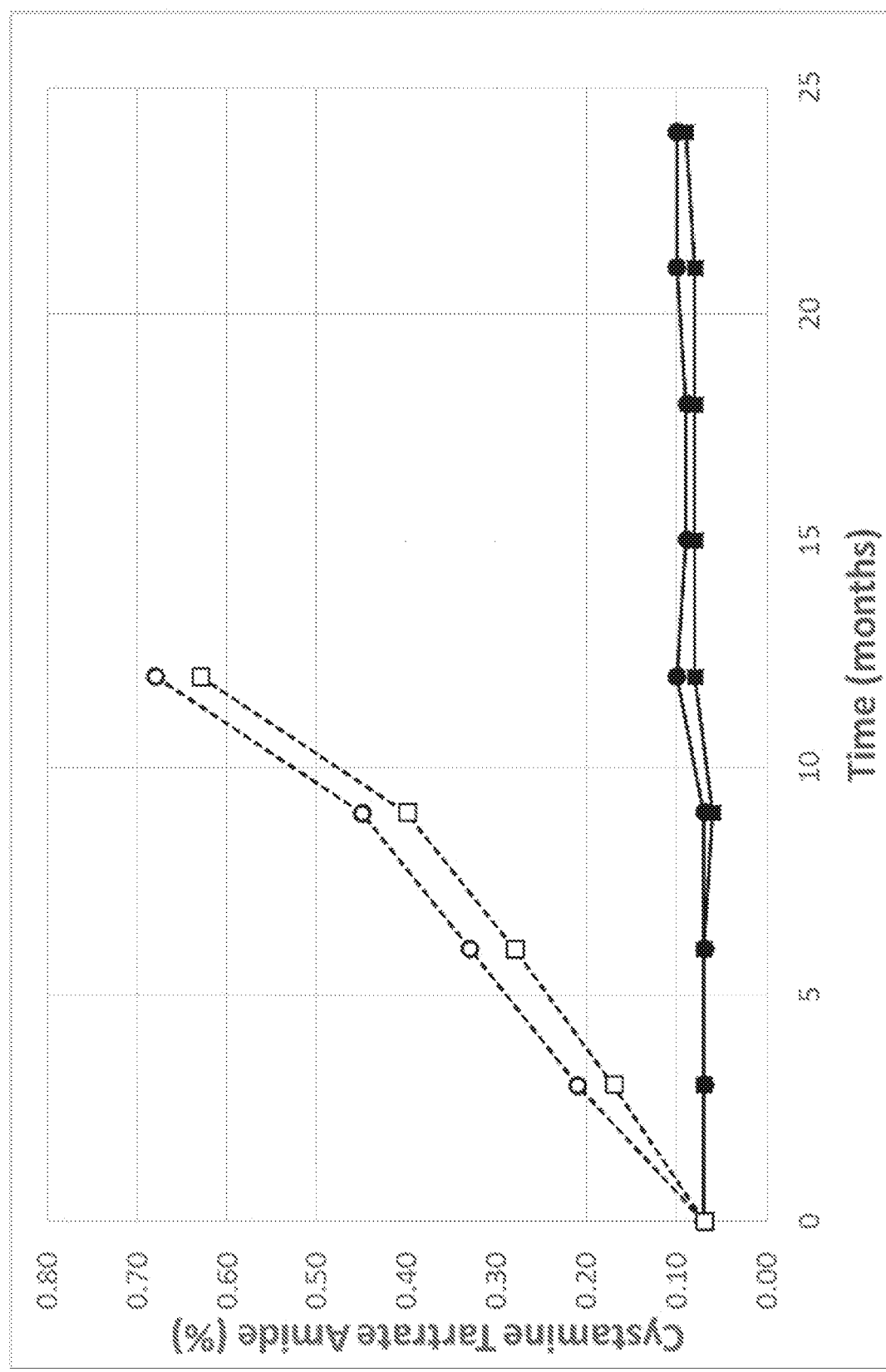
FIG. 1F shows a comparison of cold storage (2° C.-8° C.) to room temperature storage (25° C./60% RH) for cystamine tartrate amide (relative to cysteamine bitartrate; expressed as a percentage) in samples of 25-mg PROCYSBI®. Open circles and squares (○, □) with dotted lines represent 25° C./60% RH data for lots A and B, respectively. Closed circles and squares (•, ■) with solid lines represent 2° C.-8° C. data for lots A and B, respectively.
Figure 1G:
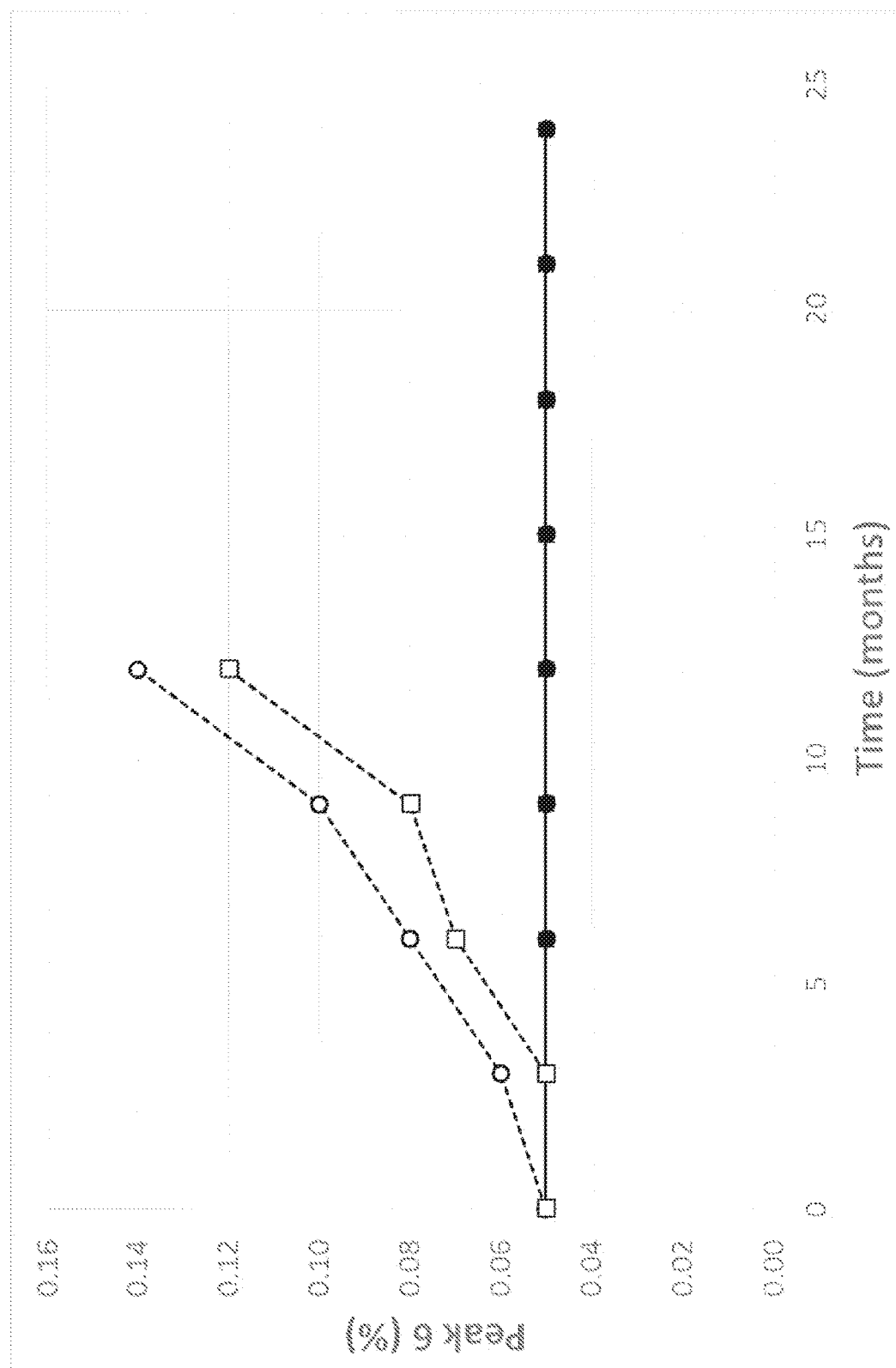
FIG. 1G shows a comparison of cold storage (2° C.-8° C.) to room temperature storage (25° C./60% RH) for Peak 6 (relative to cysteamine bitartrate; expressed as a percentage) in samples of 25-mg PROCYSBI®. Open circles and squares (○, □) with dotted lines represent 25° C./60% RH data for lots A and B, respectively. Closed circles and squares (•, ■) with solid lines represent 2° C.-8° C. data for lots A and B, respectively.
Figure 2A:
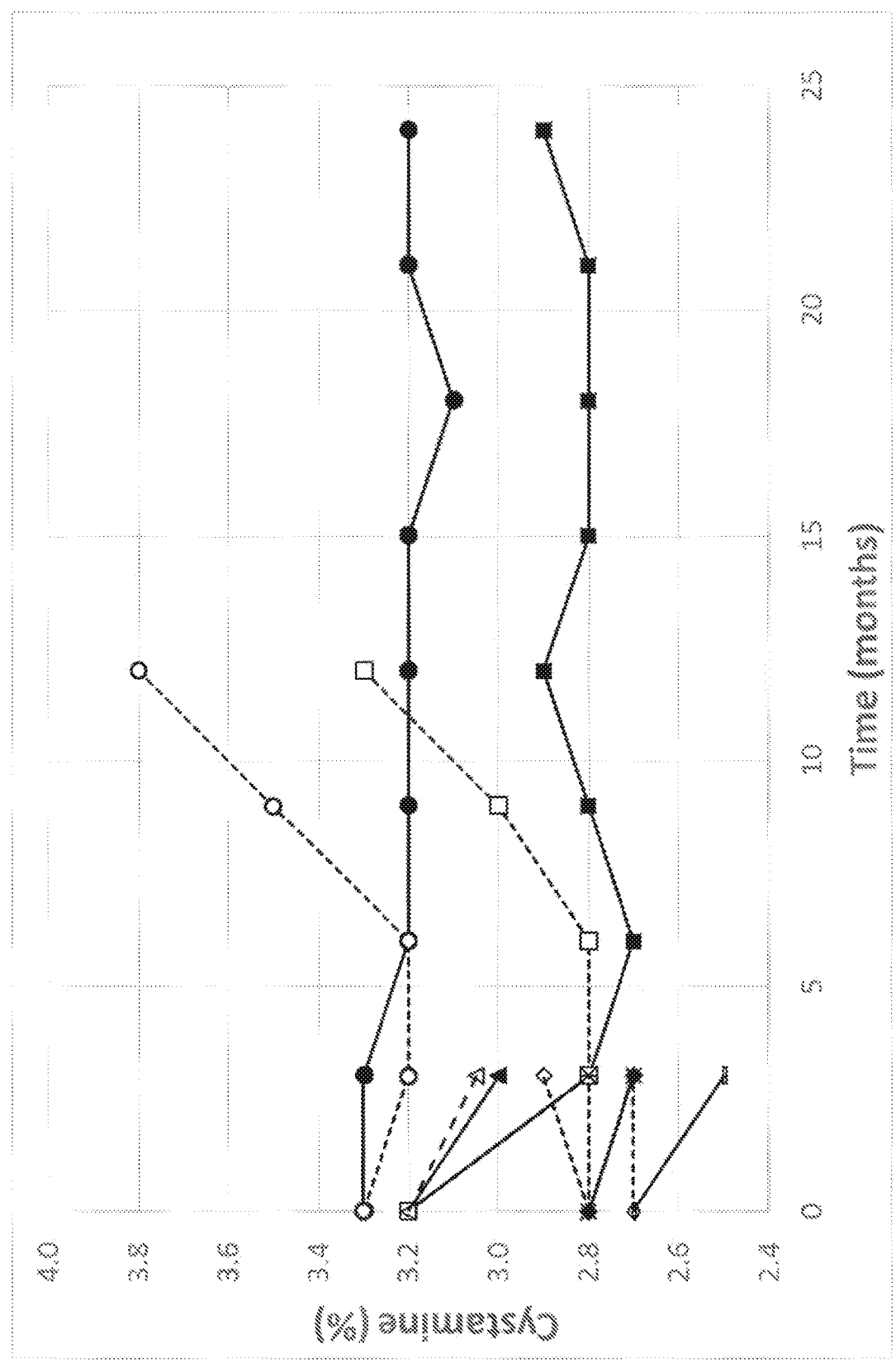
FIG. 2A shows a comparison of cold storage (2° C.-8° C.) to room temperature storage (25° C./60% RH) for cystamine (relative to cysteamine bitartrate; expressed as a percentage) in samples of 25-mg or 75-mg PROCYSBI®. Open symbols with dotted lines represent 25° C./60% RH data and closed symbols with solid lines represent 2° C.-8° C. data. Data for lots A, B, C, D, E, and F are represented by circles (○, •), squares (□, ■), triangles (Δ, ▲), diamonds (◇,◆), stars (*) and horizontal-lines (-), respectively. Values below limit of quantitation (LOQ) and not detected (ND) are shown as 0.05%, the LOQ.
Figure 2B:
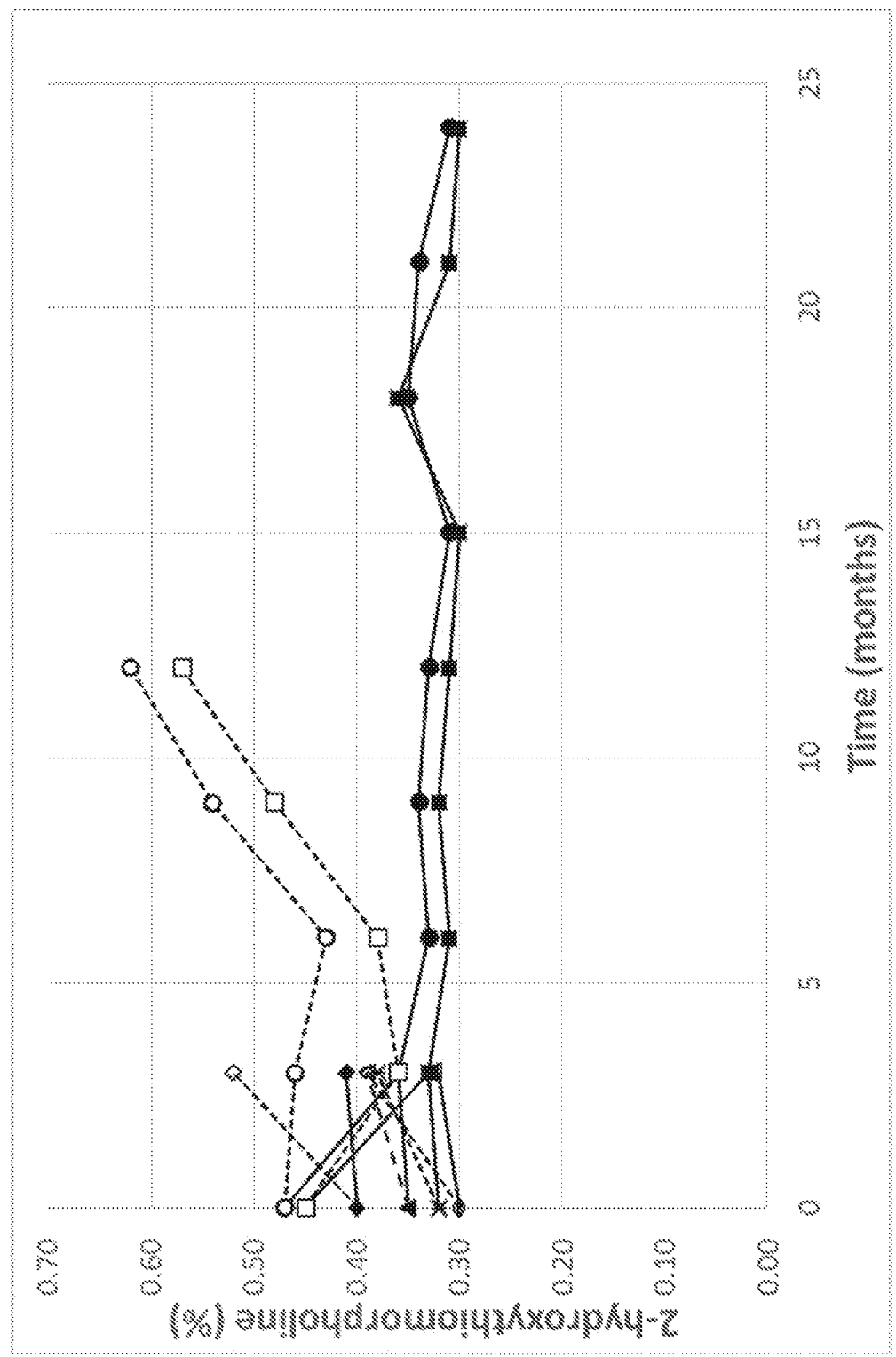
FIG. 2B shows a comparison of cold storage (2° C.-8° C.) to room temperature storage (25° C./60% RH) for 2-hydroxythiomorpholine (relative to cysteamine bitartrate; expressed as a percentage) in samples of 25-mg or 75-mg PROCYSBI®. Open symbols with dotted lines represent 25° C./60% RH data and closed symbols with solid lines represent 2° C.-8° C. data. Data for lots A, B, C, D, E and F are represented by circles (○, •), squares (□, ■), triangles (Δ, ▲), diamonds (◇,◆), stars (*) and horizontal-lines (-), respectively. Values below limit of quantitation (LOQ) and not detected (ND) are shown as 0.05%, the LOQ.
Figure 2C:
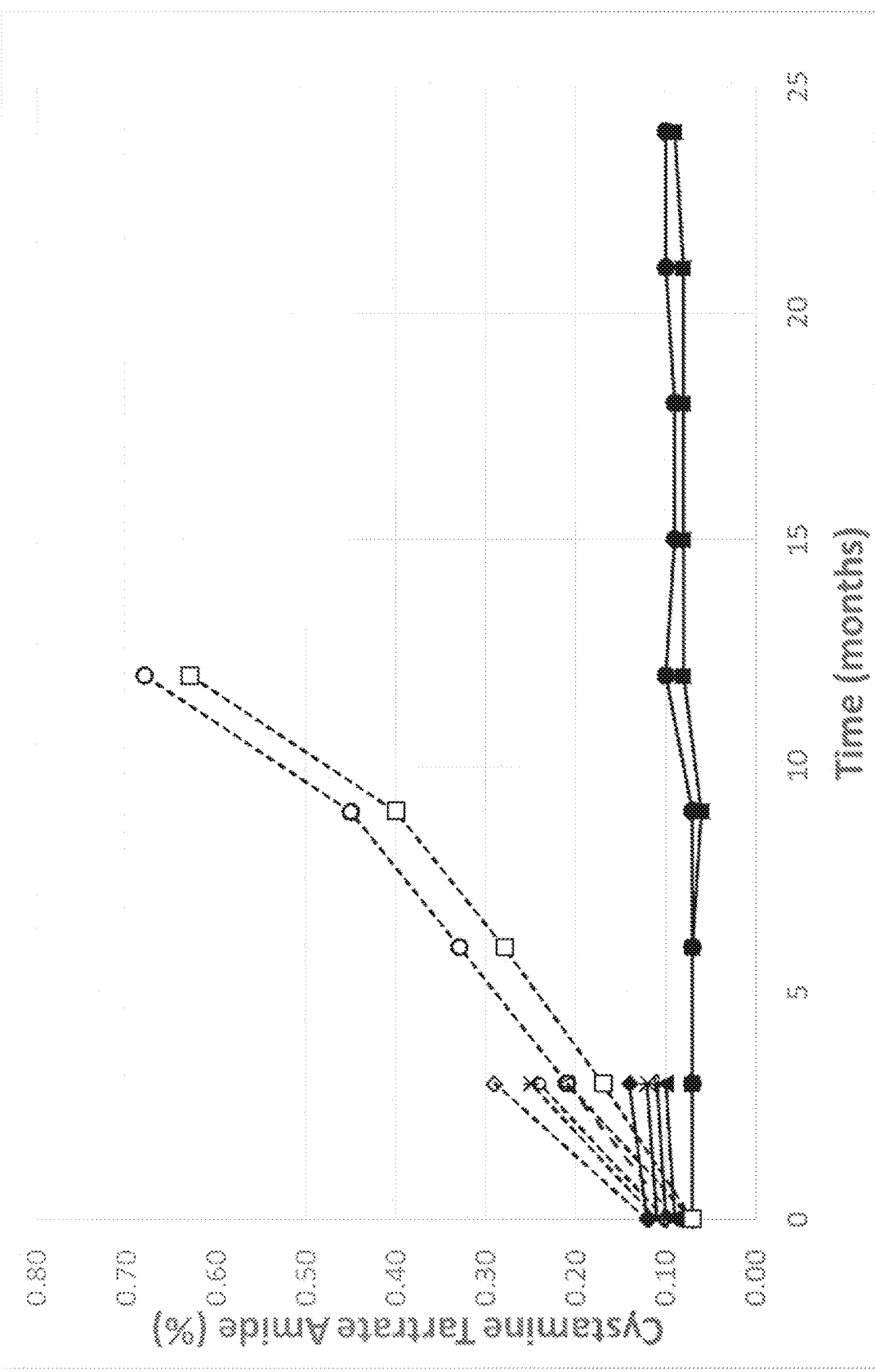
FIG. 2C shows a comparison of cold storage (2° C.-8° C.) to room temperature storage (25° C./60% RH) for cystamine tartrate amide (relative to cysteamine bitartrate; expressed as a percentage) in samples of 25-mg or 75-mg PROCYSBI®. Open symbols with dotted lines represent 25° C./60% RH data and closed symbols with solid lines represent 2° C.-8° C. data. Data for lots A, B, C, D, E and F are represented by circles (○, •), squares (□, ■), triangles (Δ, ▲), diamonds (◇,◆), stars (*) and horizontal-lines (-), respectively. Values below limit of quantitation (LOQ) and not detected (ND) are shown as 0.05%, the LOQ.
Figure 2D:
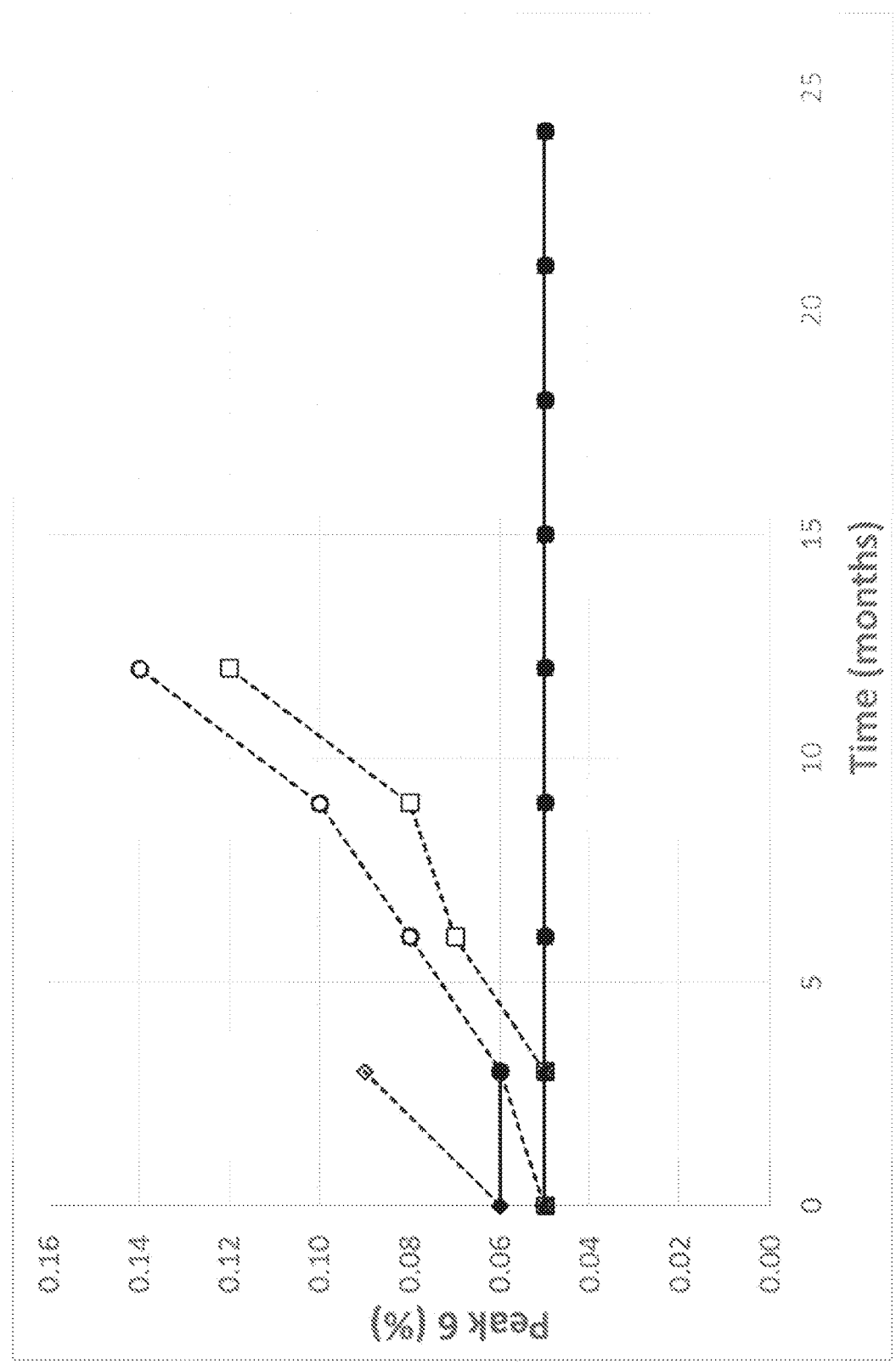
FIG. 2D shows a comparison of cold storage (2° C.-8° C.) to room temperature storage (25° C./60% RH) for Peak 6 (relative to cysteamine bitartrate expressed as a percentage) in samples of 25-mg or 75-mg PROCYSBI®. Open symbols with dotted lines represent 25° C./60% RH data and closed symbols with solid lines represent 2° C.-8° C. data. Data for lots A, B, C, D, E and F are represented by circles (○, •), squares (□, ■), triangles (Δ, ▲), diamonds (◇,◆), stars (*) and horizontal-lines (-), respectively. Values below limit of quantitation (LOQ) and not detected (ND) are shown as 0.05%, the LOQ.

FIGS. 1A-1G show long-term stability data for two lots of 25 mg PROCYSBI® (Lots A and B) stored at 2° C.-8° C./ambient RH for 24 months or at 25° C./60% RH for 12 months. Samples stored at 2° C.-8° C. were tested after storage for 3, 6, 9, 12, 15, 18, 21, and 24 months. Samples stored at 25° C. were tested after storage for 0, 3, 6, 9, 12, 15, 18, 21, and 24 months. At each time point, three 60-count bottles were taken from storage and analyzed as described above. FIG. 1A shows the amount of cysteamine bitartrate relative to the label claim of 25 mg ("Assay") (expressed as a percent), while FIGS. 1B and 1C, respectively, show acid stage dissolution and buffer stage dissolution relative to the label claim of 25 mg (expressed as a percent). FIGS. 1D-1G show the amount of the impurities cystamine, 2-hydroxythiomorpholine, cystamine tartrate amide, and Peak 6 after storage at 2° C.-8° C./ambient RH for 24 months or at 25° C./60% RH for 12 months. At 25° C./60% RH, each of the impurities increased through 12-month storage. In sharp contrast, the levels of cystamine, 2-hydroxythiomorpholine, cystamine tartrate amide, and Peak 6 exhibited little to no increases through 24 months at 2° C.-8° C. storage.

Tables 2 and 3 compare 2° C.-8° C. drug product storage with storage at 25° C./60% RH for lots A and B, respectively, for the 12 impurities that may grow on stability (cystamine, Peak A, Peak B, Peak C, 2-hydroxythiomorpholine, Peak D, cystamine tartrate amide, 2-hydroxymethylthiazolidine. Peak 5. Peak 6. Peak J, and Peak K), as well as total related substances (TRS). Tables 2 and 3 show that the levels of each of these impurities at 2° C.-8° C. exhibited little to no growth through 24 months. Tables 2 and 3 also show that the impurity levels after 18 months storage at 2° C.-8° C. were all lower than or equal to levels after only 12 months storage of 25° C./60% RH. As Tables 2 and 3 illustrate, 2° C.-8° C. storage of DP markedly reduces the rate of growth impurities relative to storage at 25° C./60% RH.

TABLE 2

Comparison of Impurities Levels for Lot A After Storage at 2° C.-8° C. and at 25° C./60% RH for Impurities That May Increase on Stability

| | Impurity Level for Lot A % | | | |
|---|---|---|---|---|
| | 2° C.-8° C. | | | 25° C./60% RH |
| Impurity | Initial | 18M | 24M | 12M |
| Cystamine | 3.3 | 3.1 | 3.2 | 3.8 |
| Peak A | ND | ND | ND | 0.10 |
| Peak B | 0.05 | 0.05 | 0.07 | 0.06 |
| Peak C | ND | ND | <0.05 | 0.05 |
| 2-hydroxythiomorpholine | 0.47 | 0.35 | 0.31 | 0.62 |
| Peak D | ND | ND | ND | 0.07 |
| Cystamine Tartrate Amide | 0.07 | 0.09 | 0.10 | 0.68 |
| 2-hydroxymethylthiazolidine | <0.05 | <0.05 | ND | 0.08 |
| Peak 5 | <0.05 | <0.05 | <0.05 | 0.11 |
| Peak 6 | <0.05 | <0.05 | <0.05 | 0.14 |
| Peak J | ND | ND | ND | 0.06 |
| Peak K | ND | ND | ND | 0.07 |
| TRS | 4.4 | 4.1 | 4.1 | 6.2 |

ND = not detected
<0.05 = detected but below LOQ (0.05%)

TABLE 3

Comparison of Impurities Levels for Lot B After Storage at 2° C.-8° C. and at 25° C./60% RH for Impurities That May Increase on Stability

| | Impurity Level for Lot B % | | | |
|---|---|---|---|---|
| | 2° C.-8° C. | | | 25° C./60% RH |
| Impurity | Initial | 18M | 24M | 12M |
| Cystamine | 3.2 | 2.8 | 2.9 | 3.3 |
| Peak A | ND | ND | ND | 0.10 |
| Peak B | <0.05 | 0.06 | 0.08 | 0.06 |
| Peak C | ND | ND | ND | <0.05 |
| 2-hydroxythiomorpholine | 0.45 | 0.36 | 0.30 | 0.57 |
| Peak D | ND | ND | <0.05 | 0.06 |
| Cystamine Tartrate Amide | 0.07 | 0.08 | 0.09 | 0.63 |
| 2-hydroxymethylthiazolidine | <0.05 | <0.05 | ND | 0.07 |
| Peak 5 | <0.05 | <0.05 | <0.05 | 0.11 |
| Peak 6 | <0.05 | <0.05 | <0.05 | 0.12 |
| Peak J | ND | ND | <0.05 | <0.05 |
| Peak K | ND | ND | ND | <0.05 |
| TRS | 4.2 | 3.8 | 4.0 | 5.5 |

ND = not detected
<0.05 = detected but below LOQ (0.05%)

FIGS. 2A-2D show the relative amounts of impurities for the two lots as above, with the addition of stability data for 4 lots (a third lot of 25 mg PROCYSBI®. Lot C, and three 75 mg lots, Lots D, E, and F) stored at 2° C.-8° C. for 3 months (i.e., 3 lots of the 25 mg strength and 3 lots of the 75 mg strength). After three months of storage, three 60-count bottles of 25 mg strength PROCYSBI® and two 250-count bottles of 75 mg strength PROCYSBI® were taken from storage and analyzed as described above. FIGS. 2A-2D show that impurity levels measured through three months in the additional samples are consistent with the trends observed in the 24-month data shown in FIGS. 1D-1G and Tables 2 and 3. Stability data for the 75 mg strength lots stored at 2° C.-8° C. are expected to trend with data from the 25 mg strength lots at 2° C.-8° C. because (i) the enteric coated beads are the same (e.g., same API, formulation, components ratios), (ii) the manufacturing process is the same; in fact, beads for 25 mg strength capsules are also encapsulated at the 75 mg strength (i.e., split batches), (iii) the packaging and product-contacting materials are the same, and (iv) the degradation products and degradation mechanisms are the same for the two dosage strengths.

Taken together, these results show that the impurities growth rates during storage of PROCYSBI® at 2° C.-8° C. are dramatically lower than those observed at 25° C./60% RH. In fact, little to no growth of impurities was observed through 24-moth storage at 2° C.-8° C. At the same time, there was no degradation in product performance as measured by Assay, Acid Stage Dissolution, or Buffer Stage Dissolution after storage at 2° C.-8° C. Thus, the lower storage temperature provides a clear improvement in product quality.

Example 3

Predicted Shelf-Life Values for PROCYSBI® when Stored at 2° C.-8° C.

Predicted shelf-life values for PROCYSBI® for storage conditions of 2° C.-8° C. were calculated using the software package SLIMStat® for the 24 months of data obtained for two lots of 25 mg PROCYSBI® (Lots A and B) (see Example 2). Table 4 shows SLIMStat® predictions for Lots A and B individually. Numeric predictions for several impurities were not available due to limited data points with values about LOQ (0.05%) over 24 months (i.e., the confidence interval did not exceed the product stability specification); these results are represented in Table 4 by the start symbol (*).

The shortest predicted shelf-life for 25 mg PROCYSBI® stored at 2° C.-8° C. was 79 months, based on Peak B for Lot B. The longest predicted shelf-life was 2,608 months (i.e., 217 years), based upon the 2-hydroxythiomorpholine results for Lot B. The shelf-life predictions based upon Assay, and Acid Stage Dissolution and Buffer Stage Dissolution varied from 39 months up to 493 months. Notably, all SLIMStat® shelf-life predictions for 2° C.-8° C. storage were far beyond the currently approved expiry of 18 months at room temperature, again illustrating the marked decrease in DP degradation with 2° C.-8° C. storage.

TABLE 4

Predicted Shelf-Life at 2° C.-8° C. Storage

| | Predicted Shelf-Life at 2° C.-8° C. (M) | |
|---|---|---|
| Test | Lot A | Lot B |
| Cystamine | * | 357 |
| Peak A | 266 | 180 |
| Peak B | 118 | 79 |
| Peak C | * | * |
| 2-hydroxythiomorpholine | * | 2608 |
| Peak D | * | * |
| Cystamine Tartrate Amide | 584 | 941 |
| 2-hydroxymethylthiazolidine | * | * |
| Peak 5 | * | * |
| Peak 6 | * | * |
| Peak J | * | * |
| Peak K | 764 | 1018 |
| Total Related Substances | * | 439 |
| Assay[a] | 48 | 39 |
| Acid Stage Dissolution | 493 | * |
| Buffer Stage Dissolution[b] | 69 | 69 |

* = Confidence interval of SLIMStat ® prediction does not exceed Specification.
[a]Based upon a lower Assay specification of 90.0%.
[b]Based upon a minimum dissolution specification of 80% within 20 minutes.

Example 4

Impurity Levels in PROCYSBI® Remain Low after Storage at 2° C.-8° C. for 15 Months Followed by Storage for 3 Months at 25° C.

Samples of PROCYSBI® were tested for chemical stability after storage at a temperature of 2° C.-8° C. for up to 15 months followed by excursions of up to 3 months at 25° C./60% RH, 30° C./65% RH, or 30° C./75% RH (18 months of total storage time). Samples were transferred from one condition to another on the same day. The methods used for storing and testing the samples were the same as those described above in Example 2.

FIGS. 3A-3H show stability data for two lots of 25 mg PROCYSBI® (Lots A and B) at 2-8° C. for 15 months followed by excursions of up 3 months at 25° C./60% RH, 30° C./65% RH, or 30° C./75% RH. Levels of the impurities cystamine (FIGS. 3A and 3B), 2-hydroxythiomorpholine (FIGS. 3C and 3D), cystamine tartrate amide (FIGS. 3E and 3F), and Peak 6 (FIGS. 3G and 3H) are shown as amount of the chemical impurity relative to the amount of cysteamine bitartrate measured in that chromatogram (i.e., the ratio of the amount of the impurity to the amount of cysteamine bitartrate, expressed as a percent). The apparent growth rates of the impurities during the 3-month step-up period generally was similar to the growth rates observed for 25 mg PROCYSBI® stored exclusively at 25° C./60% RH. FIG. 4 also shows that the levels of each of the four impurities after the 3-month step-ups (18 months total) were lower than their respective levels after only 12 months storage exclusively at 25° C./60% RH.

Tables 5 and 6 show the stability date for 25 mg PROCYSBI® Lots A and B, respectively, for the 12 impurities that may increase on stability for (a) 3-month storage at 25° C./60% RH, 30° C./65% RH and 30° C./75% RH after 15 months initial storage 2° C.-8° C., (b) 25° C./60% RH storage for 12 months, and (c) 2° C.-8° C. storage at both 15 and 18 months. As shown in Tables 5 and 6, levels of each of the impurities after the samples were transferred to and stored at higher temperatures were all nearly all lower than or equal to their respective levels after only 12 months storage exclusively at 25° C./60% RH.

TABLE 5

Results for Storage at 25° C./60% RH, 30° C./65% RH, and 30° C./75% RH After Initial Storage at 2° C.-8° C. for Lot A

| | Impurity Levels for Lot A (%) | | | | | | |
|---|---|---|---|---|---|---|---|
| | 2° C.-8° C. | | | 1.5M -> 18M Step-Ups* | | | 25° C./60% RH |
| Test | Initial | 15M | 18M | 25° C./60% | 30° C./65% | 30° C./75% | 12M |
| Cystamine | 3.3 | 3.2 | 3.1 | 3.3 | 3.2 | 3.2 | 3.8 |
| Peak A | ND | <0.05 | ND | ND | ND | ND | 0.10 |
| Peak B | 0.05 | 0.06 | 0.05 | 0.05 | 0.06 | 0.06 | 0.06 |
| Peak C | ND | ND | ND | ND | ND | ND | <0.05 |
| 2-hydroxythio-morpholine | 0.47 | 0.31 | 0.35 | 0.42 | 0.49 | 0.50 | 0.62 |
| Peak D | ND | ND | ND | ND | <0.05 | <0.05 | 0.07 |
| Cystamine Tartrate Amide | 0.07 | 0.09 | 0.09 | 0.22 | 0.42 | 0.43 | 0.68 |
| 2-hydroxymethyl-thiazolidine | <0.05 | ND | <0.05 | ND | ND | ND | 0.08 |
| Peak 5 | <0.05 | <0.05 | <0.05 | 0.05 | 0.07 | 0.08 | 0.11 |
| Peak 6 | <0.05 | 0.05 | <0.05 | 0.07 | 0.11 | 0.11 | 0.14 |
| Peak J | ND | ND | ND | ND | <0.05 | <0.05 | 0.06 |
| Peak K | ND | ND | ND | ND | ND | ND | 0.07 |
| TRS | 4.4 | 4.1 | 4.1 | 4.5 | 4.8 | 4.8 | 6.2 |

*15M storage at 2° C.-8° C. followed by 3M storage at 25° C./60% RH, 30° C./65% RH or 30° C./75% RH
< 0.05 = below LOQ
ND = not detected

TABLE 6

Results for Storage at 25° C./60% RH, 30° C./65% RH, and 30° C./75% RH After Initial Storage at 2° C.-8° C. for Lot A

| | Impurity Levels for Lot A (%) | | | | | | |
|---|---|---|---|---|---|---|---|
| | 2° C.-8° C. | | | 1.5M -> 18M Step-Ups* | | | 25° C./60% RH |
| Test | Initial | 15M | 18M | 25° C./60% | 30° C./65% | 30° C./75% | 12M |
| Cystamine | 3.2 | 2.8 | 2.8 | 2.8 | 3.0 | 2.9 | 3.3 |
| Peak A | ND | <0.05 | ND | ND | ND | ND | 0.10 |
| Peak B | <0.05 | 0.07 | 0.06 | 0.10 | 0.06 | 0.06 | 0.06 |
| Peak C | ND | ND | ND | <0.05 | ND | ND | <0.05 |
| 2-hydroxythio-morpholine | 0.45 | 0.30 | 0.36 | 0.39 | 0.48 | 0.47 | 0.57 |
| Peak D | ND | ND | ND | <0.05 | <0.05 | <0.05 | 0.06 |
| Cystamine Tartrate Amide | 0.07 | 0.08 | 0.08 | 0.21 | 0.38 | 0.39 | 0.63 |
| 2-hydroxymethyl-thiazolidine | <0.05 | ND | <0.05 | 0.05 | ND | ND | 0.07 |
| Peak 5 | <0.05 | <0.05 | <0.05 | 0.06 | 0.07 | 0.08 | 0.11 |
| Peak 6 | <0.05 | 0.05 | <0.05 | 0.06 | 0.10 | 0.10 | 0.12 |
| Peak J | ND | ND | ND | ND | <0.05 | <0.05 | <0.05 |
| Peak K | ND | ND | ND | ND | ND | ND | <0.05 |
| TRS | 4.2 | 3.8 | 3.8 | 4.1 | 4.5 | 4.4 | 5.5 |

*15M storage at 2° C.-8° C. followed by 3M storage at 25° C./60% RH, 30° C./65% RH or 30° C./75% RH
< 0.05 = below LOQ
ND = not detected Taken together. FIGS. 3A-3G and Tables 5 and 6 show that 25 mg PROCYSBI® stored at 2° C.-8° C. for 15 months, followed by storage at 25° C./60% RH for 3 additional months (18 months total time) resulted in lower levels for nearly all of the 19 measured impurities relative to 12 months storage at 25° C./60% RH. Moreover, samples tested after storage for 3 months at more stringent conditions (e.g., 30° C./65% RH and 30° C./75% RH) had lower impurity levels than samples stored for 12 months at 25° C./60% RH.

Example 5

Predicted Shelf-Life Values for PROCYSBI® when Stored at 2° C.-8° C. Followed by Storage for 4 Months at 25° C.

An extrapolation analysis was performed to evaluate 4-month storage at room temperature following 2° C.-8° C. long-term storage. Specifically, the duration of 25° C./60% RH storage required for each impurity to increase from its assumed level at release to its stability specification level as calculated.

Degradation rates for each of the 12 impurities that may increase on stability at 25° C./60% RH were determined from a date set of 10 lots (G, H, I, J, K, L, M, N, O, and P) using SLIMStat® (Table 7).

In calculating the degradation rates to be used in the extrapolation analysis, the largest individual degradation rate for each of the 12 impurities was used ("Highest Degradation Rate").

The level of each impurity at DP lot release was assumed to be close to the release specification (see ICH Guidance, Evaluation for Stability Data Q1E, 2003). Numerically, close to release specification was taken to be 80% of the release specification (e.g., for an impurity with a release specification of 0.15%, the level of that impurity upon release was taken to be 80% of 0.15%, or 0.12%). The release specifications currently approved in the US and EU are identical for the 12 impurities that may grow on stability at 25° C./60% RH. The release specifications and assumed values at release (i.e., "close" to release specifications) for the 12 impurities are shown in Table 8.

The rates of growth of impurities at 2° C.-8° C. were taken to be negligible, based upon the 24-month real-time stability results Example 2. That is, the assumed impurity levels at release were taken to be the same as values after storage at 2° C.-8° C. for up to 24 months.

Using this information, the duration of 25/60% RH storage required for each impurity to increase from its assumed level at release (i.e., 80% of the release specification to its stability specification level, $t_{Step-Up}$, was calculated with Equation 1 (assuming linear degradation kinetics).

Equation 1:

$$t_{Step-Up} = \frac{(\text{Stability Specification}) - (\text{Assumed Release Level; "Close"})}{(\text{Highest Degradation Rate})}$$

Table 8 shows the calculated $t_{Step-Up}$ values. For each of the 12 impurities that may increase on stability, the $t_{Step-Up}$ value is greater than or equal to 4 months. In summary, the extrapolation analysis indicates that PROCYSBI® can be stored at 2° C.-8° C. for 0-24 months, followed by storage for 4 months at 25° C. without resulting in high levels of impurities. Accordingly, patients would be able to store PROCYSBI®, once they receive it, at room temperature conditions for up to four months. Patient storage at refrigerated conditions is also supported through a total storage duration of at least 24 months.

TABLE 7

Degradation Rates for PROCYSBI ® at 25° C./60% RH

| Impurity | Degradation Rates (%.month) (by lot) | | | | | | | | | | |
|---|---|---|---|---|---|---|---|---|---|---|---|
| | G | H | I | J | K | L | M | N | O | P | Max. |
| Cystamine | 0.0390 | 0.0460 | 0.0296 | −0.0167 | −0.0067 | 0.0621 | 0.0369 | 0.0927 | 0.0952 | 0.0705 | 0.0952 |
| Peak A | 0.0000 | 0.0007 | 0.0006 | −0.0024 | −0.0026 | 0.0017 | 0.0005 | 0.0028 | 0.0031 | 0.0005 | 0.0031 |
| Peak B | 0.0082 | 0.0056 | 0.0041 | 0.0030 | 0.0017 | 0.0023 | 0.0029 | 0.0043 | 0.0037 | 0.0050 | 0.0082 |
| Peak C | 0.0005 | 0.0008 | 0.0004 | 0.0000 | 0.0000 | 0.0010 | 0.0000 | 0.0042 | 0.0035 | 0.0010 | 0.0042 |
| 2-hydroxythio-morpholine | 0.0226 | 0.0202 | 0.0145 | 0.0217 | 0.0127 | 0.0286 | 0.0182 | 0.0372 | 0.0343 | 0.0288 | 0.0372 |
| Peak D | 0.0052 | 0.0053 | 0.0052 | 0.0000 | 0.0000 | 0.0045 | 0.0019 | 0.0133 | 0.0105 | 0.0066 | 0.0133 |
| Cystamine Tartrate Amide | 0.0539 | 0.0566 | 0.0542 | 0.0543 | 0.0587 | 0.0700 | 0.0505 | 0.0690 | 0.0694 | 0.0487 | 0.0700 |
| 2-hydroxymethyl-thiazolidine | 0.0087 | 0.0065 | 0.0056 | 0.0007 | 0.0000 | 0.0078 | 0.0052 | 0.0114 | 0.0110 | 0.0074 | 0.0114 |
| Peak 5 | 0.0055 | 0.0047 | 0.0046 | 0.0013 | 0.0000 | 0.0087 | 0.0065 | 0.0095 | 0.0095 | 0.0060 | 0.0095 |
| Peak 6 | 0.0093 | 0.0068 | 0.0068 | 0.0020 | 0.0033 | 0.0106 | 0.0051 | 0.0215 | 0.0181 | 0.0104 | 0.0215 |
| Peak J | 0.0029 | 0.0023 | 0.0012 | 0.0000 | 0.0000 | 0.00211 | 0.0020 | 0.0098 | 0.0072 | 0.0054 | 0.0098 |
| Peak K | 0.0026 | 0.0012 | 0.0002 | 0.0010 | 0.0000 | 0.0005 | 0.0000 | 0.0019 | 0.0015 | 0.0000 | 0.0026 |
| TRS | 0.1367 | 0.1367 | 0.1527 | 0.0367 | 0.0700 | 0.2190 | 0.1638 | 0.3053 | 0.2914 | 0.0373 | 0.3053 |

TABLE 8

Extrapolation Analysis of 4-Month Step-Ups To 25° C./60% RH Storage

| Impurity | Specifications (%) | | | Highest Deg Rate (%/month) | $t_{Step-Up}$ (months) | Supports 4M Step-Up to 25° C. |
|---|---|---|---|---|---|---|
| | Release | Close* | Stability | | | |
| Cystamine | 4.0 | 3.2 | 5.0 | 0.0952 | 19 | Yes |
| Peak A | 0.20 | 0.16 | 0.20 | 0.0031 | 13 | Yes |
| Peak B | 0.15 | 0.12 | 0.15 | 0.0082 | 4 | Yes |
| Peak C | 0.10 | 0.08 | 0.10 | 0.0042 | 5 | Yes |
| 2-hydroxythio-morpholine | 0.50 | 0.40 | 1.0 | 0.0372 | 16 | Yes |
| Peak D | 0.10 | 0.08 | 0.30 | 0.0133 | 17 | Yes |
| Cystamine Tartrate Amide | 0.15 | 0.12 | 1.3 | 0.0700 | 17 | Yes |
| 2-hydroxymethyl-thiazolidine | 0.10 | 0.08 | 0.3 | 0.0114 | 19 | Yes |
| Peak 5 | 0.10 | 0.08 | 0.30 | 0.0095 | 23 | Yes |
| Peak 6 | 0.10 | 0.08 | 0.30 | 0.0215 | 10 | Yes |
| Peak J | 0.10 | 0.08 | 0.15 | 0.0098 | 7 | Yes |
| Peak K | 0.10 | 0.08 | 0.15 | 0.0026 | 27 | Yes |
| TRS | 5.0 | 4.0 | 8.0 | 0.3053 | 13 | Yes |

*Close to Release Specification = 80% * (Release Specification)

The various embodiments described above can be combined to provide further embodiments. All of the U.S. patents, U.S. patent application publications. U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of treating nephropathic cystinosis in a subject in need thereof, comprising:
administering twice daily to the subject an oral pharmaceutical composition comprising cysteamine bitartrate,
wherein the oral pharmaceutical composition contains 2-hydroxythiomorpholine in an amount less than 0.5% relative to the amount of cysteamine bitartrate,
wherein the oral pharmaceutical composition was stored by a manufacturer, a distributor, a pharmacy, or a hospital at a temperature of between about 2° C. and about 8° C. prior to dispensing the oral pharmaceutical composition to the subject, and
wherein after the oral pharmaceutical composition is dispensed to the subject, the oral pharmaceutical composition is stored at a temperature of between about 20° C. and about 25° C.

2. The method according to claim 1, wherein the oral pharmaceutical composition further comprises an enteric coating wherein the enteric coating comprises poly(methacrylic acid co-ethyl acrylate) 1:1.

3. The method according to claim 1, wherein the oral pharmaceutical composition contains 2-hydroxythiomorpholine in an amount less than 0.5% relative to the amount of cysteamine bitartrate when the oral pharmaceutical composition is stored at a temperature of between about 2° C. and about 8° C. for a period of up to 15 months.

4. The method according to claim 1, wherein the oral pharmaceutical composition contains 2-hydroxythiomorpholine in an amount less than 0.5% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 25° C. and 60% relative humidity for a period of up to 3 months.

5. The method according to claim 1, wherein the oral pharmaceutical composition contains 2-hydroxythiomorpholine in an amount less than 0.5% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 30° C. and 65% relative humidity for a period of up to 3 months.

6. The method according to claim 1, wherein the oral pharmaceutical composition contains 2-hydroxythiomorpholine in an amount less than 0.5% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 30° C. and 70% relative humidity for a period of up to 3 months.

7. A method of treating nephropathic cystinosis in a subject in need thereof, comprising:
administering twice daily to the subject an oral pharmaceutical composition comprising cysteamine bitartrate,
wherein the oral pharmaceutical composition contains cystamine in an amount less than 4% relative to the amount of cysteamine bitartrate,
wherein the oral pharmaceutical composition was stored by a manufacturer, a distributor, a pharmacy, or a hospital at a temperature of between about 2° C. and about 8° C. prior to dispensing the oral pharmaceutical composition to the subject, and
wherein after the oral pharmaceutical composition is dispensed to the subject, the oral pharmaceutical composition is stored at a temperature of between about 20° C. and about 25° C.

8. The method according to claim 7, wherein the oral pharmaceutical composition further comprises an enteric coating, wherein the enteric coating comprises poly(methacrylic acid co-ethyl acrylate) 1:1.

9. The method according to claim 7, wherein the oral pharmaceutical composition contains cystamine in an amount less than 4% relative to the amount of cysteamine bitartrate when the oral pharmaceutical composition is stored at a temperature of between about 2° C. and about 8° C. for a period of up to 15 months.

10. The method according to claim 7, wherein the oral pharmaceutical composition contains cystamine in an amount less than 4% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 25° C. and 60% relative humidity for a period of up to 3 months.

11. The method according to claim 7, wherein the oral pharmaceutical composition contains cystamine in an amount less than 4% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 30° C. and 65% relative humidity for a period of up to 3 months.

12. The method according to claim 7, wherein the oral pharmaceutical composition contains cystamine in an amount less than 4% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 30° C. and 70% relative humidity for a period of up to 3 months.

13. A method of treating nephropathic cystinosis in a subject in need thereof, comprising:
administering twice daily to the subject an oral pharmaceutical composition comprising cysteamine bitartrate, wherein the pharmaceutical composition contains cystamine tartrate amide in an amount less than 0.5% relative to the amount of cysteamine bitartrate,
wherein the oral pharmaceutical composition was stored by a manufacturer, a distributor, a pharmacy, or a hospital at a temperature of between about 2° C. and about 8° C. prior to dispensing the oral pharmaceutical composition to the subject, and
wherein after the oral pharmaceutical composition is dispensed to the subject, the oral pharmaceutical composition is stored at a temperature of between about 20° C. and about 25° C.

14. The method according to claim 13, wherein the oral pharmaceutical composition further comprises an enteric coating, wherein the enteric coating comprises poly(methacrylic acid co-ethyl acrylate) 1:1.

15. The method according to claim 13, wherein the oral pharmaceutical composition contains cystamine tartrate amide in an amount less than 0.5% relative to the amount of cysteamine bitartrate when the oral pharmaceutical composition is stored at a temperature of between about 2° C. and about 8° C. for a period of up to 15 months.

16. The method according to claim 13, wherein the oral pharmaceutical composition contains cystamine tartrate amide in an amount less than 0.5% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 25° C. and 60% relative humidity for a period of up to 3 months.

17. The method according to claim 13, wherein the oral pharmaceutical composition contains cystamine tartrate amide in an amount less than 0.5% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 30° C. and 65% relative humidity for a period of up to 3 months.

18. The method according to claim 13, wherein the oral pharmaceutical composition contains cystamine tartrate amide in an amount less than 0.5% relative to the amount of cysteamine bitartrate when the oral pharmaceutical composition is stored at a temperature of between about 2° C. and about 8° C. for an initial period of up to 15 months, and wherein the oral pharmaceutical composition is subsequently stored at a temperature of 30° C. and 70% relative humidity for a period of up to 3 months.

* * * * *